US012810970B2

(12) United States Patent
Issenberg et al.

(10) Patent No.: US 12,810,970 B2
(45) Date of Patent: Nov. 24, 2026

(54) METHODS, SYSTEMS, APPARATUSES, AND DEVICES FOR FACILITATING PRESENTATION OF MEDICAL DATA

(71) Applicant: Endoverse LLC, Miami, FL (US)

(72) Inventors: Saul Barry Issenberg, Pembroke Pines, FL (US); Amar Deshpande, Davie, FL (US); Daniel Sussman, Miami, FL (US); Nathaniel Ernstoff, Pompano Beach, FL (US)

(73) Assignee: Endoverse LLC, Miami, FL (US)

( * ) Notice: Subject to any disclaimer, the term of this patent is extended or adjusted under 35 U.S.C. 154(b) by 0 days.

(21) Appl. No.: 18/778,753

(22) Filed: Jul. 19, 2024

(65) Prior Publication Data

US 2025/0029686 A1 Jan. 23, 2025

Related U.S. Application Data

(60) Provisional application No. 63/514,381, filed on Jul. 19, 2023.

(51) Int. Cl.
*G16H 10/00* (2018.01)
*G02B 27/00* (2006.01)
(Continued)

(52) U.S. Cl.
CPC ......... *G16H 10/00* (2018.01); *G02B 27/0093* (2013.01); *G02B 27/017* (2013.01);
(Continued)

(58) Field of Classification Search
None
See application file for complete search history.

(56) References Cited

U.S. PATENT DOCUMENTS 10,521,603 B2 12/2019 Dascola et al.
10,616,565 B2 4/2020 Cheung
(Continued)

FOREIGN PATENT DOCUMENTS

EP 4064699 A1 9/2022
JP 2022509460 A * 1/2022
(Continued)

OTHER PUBLICATIONS

Mewes, A., Saalfeld, P., Riabikin, O. et al. A gesture-controlled projection display for CT-guided interventions. Int J Cars 11, 157-164 (2016). https://doi.org/10.1007/s11548-015-1215-0 (Year: 2015).*

*Primary Examiner* — Lena Najarian
(74) *Attorney, Agent, or Firm* — Levine Bagade Han LLP

(57) ABSTRACT

An apparatus for facilitating presentation of medical data is disclosed. Accordingly, the apparatus includes at least one of a microphone and a hand tracking device, a storage device configured for storing at least one medical data, a processing device communicatively coupled with at least one of the microphone and the hand tracking device configured for analyzing at least one of the sound data and the gesture data, generating an instruction. At least one of the head-mountable device, the ophthalmic device, and an implantable device communicatively coupled with each of the processing device and the storage device. Further, each of the head-mountable device, the ophthalmic device, and the implantable device includes at least one of a display device and a sound production device. Further, at least one of the head-mountable device, the ophthalmic device, and the implantable device is configured for presenting the at least one medical data.

15 Claims, 20 Drawing Sheets

(51) Int. Cl.

| | |
|---|---|
| ***G02B 27/01*** | (2006.01) |
| ***G06F 3/01*** | (2006.01) |
| ***G06F 3/0482*** | (2013.01) |
| ***G06F 3/16*** | (2006.01) |

(52) U.S. Cl.

CPC .............. *G06F 3/012* (2013.01); *G06F 3/013* (2013.01); *G06F 3/014* (2013.01); *G06F 3/017* (2013.01); *G06F 3/0482* (2013.01); *G06F 3/167* (2013.01)

(56) References Cited

U.S. PATENT DOCUMENTS

| | | | | |
|---|---|---|---|---|
| 10,852,838 | B2 | 12/2020 | Bradski et al. | |
| 11,297,304 | B2 | 4/2022 | Oonishi et al. | |
| 11,662,592 | B2 | 5/2023 | Zhang et al. | |
| 2014/0062900 | A1* | 3/2014 | Kaula | G16Z 99/00<br>345/173 |
| 2014/0135588 | A1* | 5/2014 | Al-Ali | G16H 40/63<br>600/300 |
| 2016/0034058 | A1* | 2/2016 | Stauber | H04N 21/4122<br>345/173 |
| 2016/0225192 | A1* | 8/2016 | Jones | G06F 3/017 |
| 2017/0323069 | A1* | 11/2017 | Bates | G16H 40/63 |
| 2018/0055386 | A1* | 3/2018 | Zielinski | A61B 5/08 |
| 2019/0099226 | A1* | 4/2019 | Hallen | A61B 34/10 |
| 2020/0159871 | A1* | 5/2020 | Bowen | G06T 11/60 |
| 2021/0165555 | A1 | 6/2021 | Holz et al. | |
| 2021/0169417 | A1* | 6/2021 | Burton | A61B 5/4857 |
| 2021/0377505 | A1* | 12/2021 | Liu | H04N 13/246 |
| 2021/0386504 | A1 | 12/2021 | Chen et al. | |
| 2022/0197029 | A1 | 6/2022 | Tornéus | |
| 2023/0360442 | A1* | 11/2023 | Soryal | G08B 21/02 |

FOREIGN PATENT DOCUMENTS

| | | | | |
|---|---|---|---|---|
| WO | WO-2019170872 | A1 * | 9/2019 | A61F 9/08 |
| WO | 2020084625 | A1 | 4/2020 | |
| WO | 2022072675 | A1 | 4/2022 | |

* cited by examiner

METHODS, SYSTEMS, APPARATUSES, AND DEVICES FOR FACILITATING PRESENTATION OF MEDICAL DATA

FIELD OF THE INVENTION

Generally, the present disclosure relates to the field of data processing. More specifically, the present disclosure relates to methods, systems, apparatuses, and devices for facilitating presentation of medical data.

BACKGROUND OF THE INVENTION

The field of data processing is technologically important to several industries, business organizations, and/or individuals. In particular, the use of data processing is prevalent for facilitating presentation of medical data.

In medical applications, computer-assisted navigation affords clinicians the advantage of an enhanced visualization of medical instruments in relation to the radiographic images of the patient's anatomical structures. Additional patient data, such as vital signs and ultrasound images, are typically made in disparate locations with the procedure room. However, a clinician's line of sight to these physical monitors may become hindered by intervening personnel or equipment during a procedure. This situation underscores the existing need for improved accessibility to comprehensive medical imaging and patient data.

Numerous electronic devices are equipped with input and output capabilities. These can include a display and keyboard for accepting user inputs and displaying content. However, existing techniques that use one device to supplement the input and output capabilities of another device may exhibit limitations with respect to efficiency, usability, or capability for user experiences. Existing techniques for facilitating the manipulation of multiple data displays shown in a display device are lacking in several respects. For instance, current technologies do not support voice-based manipulation of augmented or virtual reality type monitor(s) in a heads-up display (HUD) of information corresponding to the data shown on actual monitors in a procedural or surgical room.

Existing techniques for facilitating presentation of medical data are deficient with regard to several aspects. For instance, current technologies do not present a medical data in front of user's eyes. As a result, a different technology is needed which presents the medical data in front of user's eyes. Furthermore, current technologies do not allow users to change the user interface of heads up display. As a result, a different technology is needed which allows users to change the user interface of heads up display. Moreover, current technologies do not allow users to store a medical data. As a result, a different technology is needed which allows users to store the medical data.

Therefore, there is a need for improved methods, systems, apparatuses, and devices for facilitating presentation of medical data that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is an apparatus for facilitating presentation of medical data, in accordance with some embodiments. Accordingly, the apparatus may include at least one of a microphone and a hand tracking device. Further, the microphone may be configured for generating a sound data and the hand tracking device may be configured for generating a gesture data based on a hand gesture. Further, the apparatus may include a storage device configured for storing at least one medical data. Further, the apparatus may include a processing device communicatively coupled with at least one of the microphone and the hand tracking device. Further, the processing device may be configured for analyzing at least one of the sound data and the gesture data. Further, the processing device may be configured for generating an instruction based on the analyzing. Further, the processing device may be configured for performing at least one operation on the at least one medical data based on the instruction. Further, the at least one operation may include at least one of causing presenting of the at least one medical data and manipulating of the at least one medical data on at least one of a head-mountable device, an ophthalmic device, and an implantable device. Further, the apparatus may include at least one of the head-mountable device, the ophthalmic device, and the implantable device communicatively coupled with each of the processing device and the storage device. Further, each of the head-mountable device, the ophthalmic device, and the implantable device may include at least one of a display device and a sound production device. Further, at least one of the head-mountable device, the ophthalmic device, and the implantable device may be configured for presenting the at least one medical data based on the performing of the at least one operation.

Further, disclosed herein is an apparatus for facilitating presentation of medical data, in accordance with some embodiments. Accordingly, the apparatus may include at least one of a microphone and a hand tracking device. Further, the microphone may be configured for generating a sound data and the hand tracking device may be configured for generating a gesture data based on a hand gesture. Further, the hand tracking device may include a motion tracking glove configured for generating the gesture data by tracking the hand gesture of a user associated with the apparatus. Further, the apparatus may include a storage device configured for storing at least one medical data. Further, the apparatus may include a processing device communicatively coupled with at least one of the microphone and the hand tracking device. Further, the processing device may be configured for analyzing at least one of the sound data and the gesture data. Further, the processing device may be configured for generating an instruction based on the analyzing. Further, the processing device may be configured for performing at least one operation on the at least one medical data based on the instruction. Further, the at least one operation may include at least one of causing presenting of the at least one medical data and manipulating of the at least one medical data on at least one of a head-mountable device, an ophthalmic device, and an implantable device. Further, the apparatus may include at least one of the head-mountable device, the ophthalmic device, and the implantable device communicatively coupled with each of the processing device and the storage device. Further, each of the head-mountable device, the ophthalmic device, and the implantable device may include at least one of a display device and a sound production device. Further, at least one of the head-mountable device, the ophthalmic device, and the implantable device may be configured for presenting the at least one medical data based on the performing of the at least one operation.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
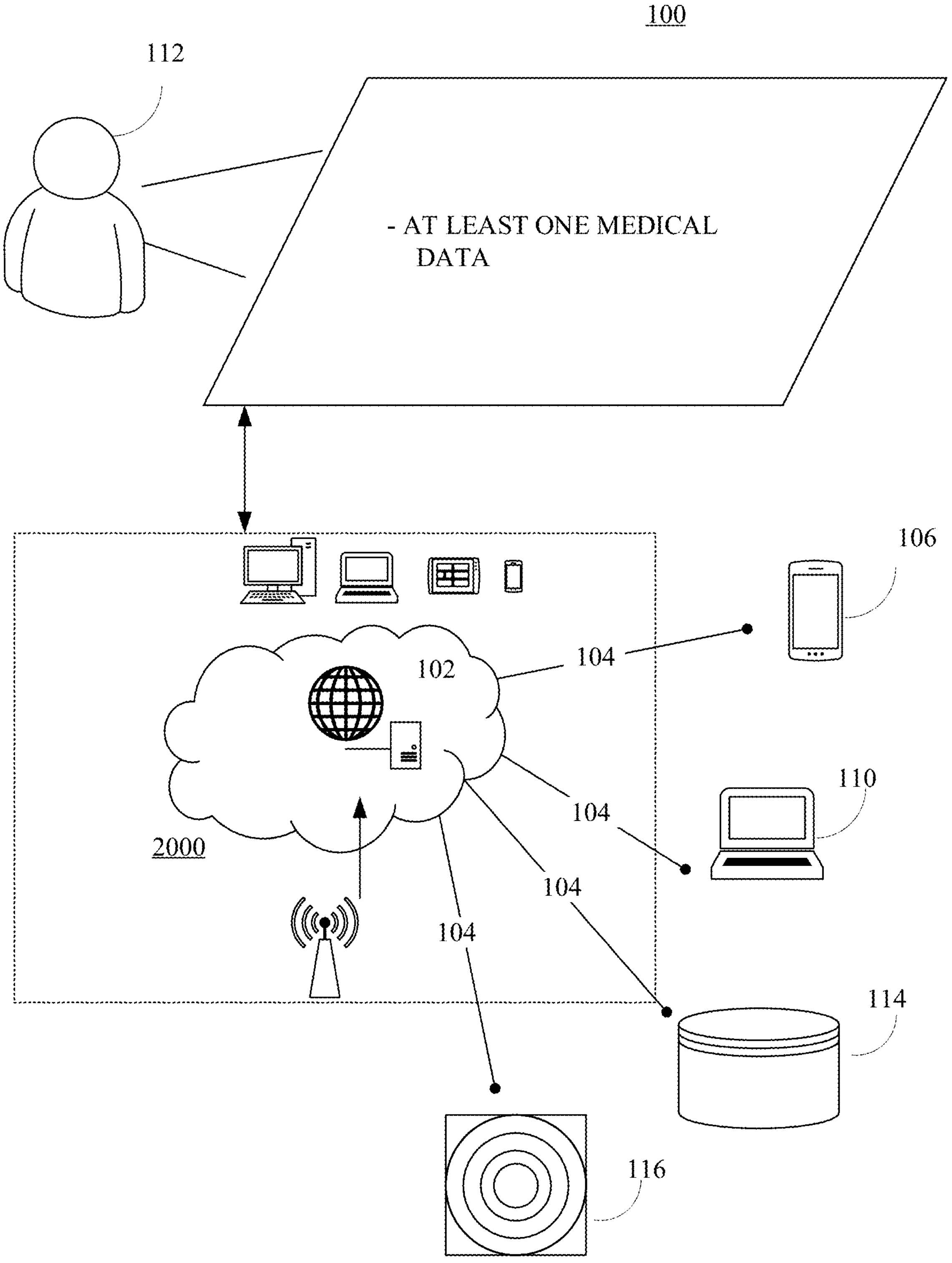
FIG. 1 is an illustration of an platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being “preferred” is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term-differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods, systems, apparatuses, and devices for facilitating presentation of medical data, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smartphone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, a public database, a private database, and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled, and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal, or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable data (e.g. username, password, passphrase, PIN, secret question, secret answer, etc.) and/or possession of a machine readable secret data (e.g. encryption key, decryption key, bar codes, etc.) and/or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.).

Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera, and so on. Likewise, the one or more steps may include receiving, using the communication device, the one or more embodied characteristics from one or more biometric sensors.

Further, one or more steps of the method may be automatically initiated, maintained, and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device, etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data, and any intermediate data there between corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes methods, systems, apparatuses, and devices for facilitating presentation of medical data.

Further, the present disclosure describes methods, systems, and apparatuses designed to facilitate the manipulation of multiple data displays presented on a display device as determined by user commands. Further, the disclosed system may be configured to support voice manipulation of augmented or virtual reality type monitor(s) in a heads-up display (HUD) of information relating to the data displayed on physical monitors in a procedure or surgical room. Further, the disclosed system may provide virtual options created using the Voice Engine system. Further, a HUD layout linked to the HUD includes full data streams from devices and selectively cropped segments of patient data streams from a device. Further, the disclosed system may be associated with a data display extraction editor that crops specific parts of an image and positions them on a virtual screen in user-customizable places. These sections can be relocated using voice commands and/or virtual hands within the virtual monitor.

Further, the disclosed system may be configured for manipulation by voice commands of multiple different data displays presented in one augmented or virtual reality type HUD monitor, and/or one PC/laptop monitor display. Further, the system may include a monitor-virtualization device, such as a head-mountable device, (or an ophthalmic device or an intraocular implant,) that may render a virtual monitor in augmented, virtual, or mixed reality. Further, a user may use voice commands to move, resize, and change screen inputs. The user may extract using the data display extraction editor relevant information from a device's display and insert the cropped data into the HUD. The position of the cropped data may be customized by the user on the PC and/or in the virtual display by voice commands and/or virtual hands.

Further, the user may use voice commands to identify and select areas of interest on the input video showing on the main virtual screen and record these areas by taking snapshots and or short videos. The recordings taken during a procedure may be stored on files on the system's computer.

The disclosed system incorporates a voice recognition training system that is self-learning. Further, the disclosed system may be based on accepting unknown words that may be used during a medical procedure, and identifying when the words are an alias for a recognized term. Further, such aliases may be then stored in a user database so that the aliases may be immediately acted on if they are detected in the future.

Further, the present disclosure describes medical devices and systems attached to a head-mounted display that manipulates multiple virtual screen inputs from such medical devices using voice commands, in general, and to voice activation methods and systems for recording information from user voice commands related to said virtual screen video feed overlaid in particular. Further, the disclosed system may be associated with customizable option prompts that control the modes (size, position in screen, world space position relative to the user) and relevant parts of each data feed comprising the virtual screen.

Further, the disclosed system may be configured for generating, interacting, and recording snapshots selected by a user with a virtual and/or real interface in the head-mounted display system or on a computer.

Further, disclosed herein is a method for facilitating manipulation of multiple data displays shown in a display device based on user commands. Accordingly, the method may include transmitting, using a communication device, at least one multimedia content to at least one device. Further, the at least one device may include a presentation device such as a heads-up display device, a monitor, a LED screen, etc. Further, the heads-up display may include an augmented reality monitor and a virtual reality monitor.

Further, the method may include receiving, using the communication device, at least one sensor data from at least one sensor. Further, the at least one sensor may include an audio sensor, a gesture sensor, an orientation sensor, a gyroscope, a motion sensor, an image sensor, etc. Further, the at least one sensor may be configured for generating the at least one sensor data based on detecting a user command. Further, the user command may be a voice command, a hand gesture, etc.

Further, the method may include analyzing, using a processing device, the at least one sensor device, and the at least one multimedia content. Further, the analyzing may include analyzing the at least one sensor device and the at least one multimedia content using at least one machine learning model. Further, the at least one machine learning model may include a natural language processing model.

Further, the method may include modifying, using the processing device, the at least one multimedia content.

Further, the method may include generating, using the processing device, at least one modified multimedia content based on the modifying.

Further, the method may include transmitting, using the communication device, at least one modified multimedia content to the at least one device.

Further, the method may include storing, using a storage device, the at least one sensor data, the at least one multimedia content, and the at least one modified multimedia content.

Further, disclosed herein is a system for facilitating manipulation of multiple data displays shown in a display device based on user commands. Accordingly, the system may include a communication device configured for transmitting at least one multimedia content to at least one device. Further, the at least one device may include a presentation device such as a heads-up display device, a monitor, a LED screen, etc. Further, the heads-up display may include an augmented reality monitor and a virtual reality monitor. Further, the communication device may be configured for receiving at least one sensor data from at least one sensor. Further, the at least one sensor may include an audio sensor, a gesture sensor, an orientation sensor, a gyroscope, a motion sensor, an image sensor, etc. Further, the communication device may be configured for transmitting at least one modified multimedia content to the at least one device.

Further, the system may include a processing device configured for analyzing the at least one sensor device and the at least one multimedia content. Further, the analyzing may include analyzing the at least one sensor device and the at least one multimedia content using at least one machine learning model. Further, the at least one machine learning model may include a natural language processing model. Further, the processing device may be configured for modifying the at least one multimedia content. Further, the processing device may be configured for generating the at least one modified multimedia content based on the modifying.

Further, the system may include a storage device configured for storing, the at least one sensor data, the at least one multimedia content, and the at least one modified multimedia content.

Further, the present disclosure includes many aspects and features. Moreover, while many aspects and features relate to, and are described in the context of methods, systems, and apparatuses for facilitating manipulation of multiple data displays shown in a display device based on user commands, embodiments of the present disclosure are not limited to use only in this context.

Further, the present disclosure describes a method for facilitating manipulation of multiple data displays presented on a display device based on user commands. Accordingly, the method may include transmitting, using a communication device, at least one multimedia content to at least one device. Further, the method may include receiving, using the communication device, at least one sensor data from at least one sensor. Further, the method may include analyzing, using a processing device, the at least one sensor device, and the at least one multimedia content. Further, the method may include modifying, using the processing device, the at least one multimedia content. Further, the method may include generating, using the processing device, at least one modified multimedia content based on the modifying. Further, the method may include transmitting, using the communication device, at least one modified multimedia content to the at least one device. Further, the method may include storing, using a storage device, the at least one sensor data, the at least one multimedia content, and the at least one modified multimedia content.

FIG. 1 is an illustration of a platform 100 consistent with various embodiments of the present disclosure. By way of non-limiting example, the platform 100 to facilitate presentation of medical data may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, and sensors 116 over a communication network 104, such as, but not limited to the Internet. Further, users of the platform 100 may include relevant parties such as, but not limited to, end-users, administrators, service providers, service consumers, and so on. Accordingly, in some instances, electronic devices operated by the one or more relevant parties may be in communication with the platform.

A user 112, such as the one or more relevant parties, may access the platform 100 through a software application or browser. The software application may be embodied as, for example, but not be limited to, a website, a web application, a desktop application, and a mobile application compatible with a computing device 2000.

Figure 2:
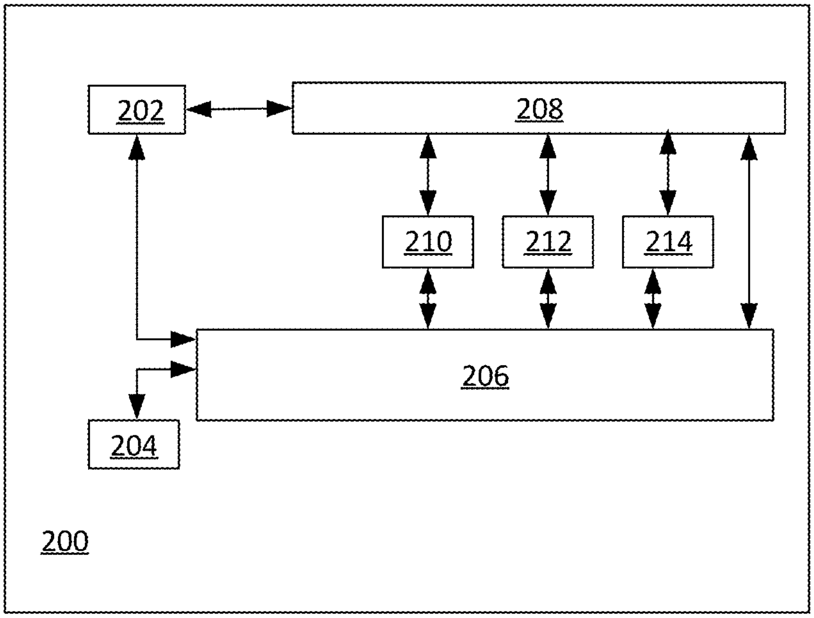
FIG. 2 is a block diagram of an apparatus 200 for facilitating presentation of medical data, in accordance with some embodiments.

FIG. 2 is a block diagram of an apparatus 200 for facilitating presentation of medical data, in accordance with some embodiments. Accordingly, the apparatus 200 may include at least one of a microphone 202 and a hand tracking device 204. Further, the microphone 202 may be configured for generating a sound data and the hand tracking device 204 may be configured for generating a gesture data based on a hand gesture. Further, used herein, the apparatus 200 may include a combination of one or more tangible devices configured to co-operate with each other to perform one or more functions. In some embodiments, the apparatus 200 may include a network of devices communicatively coupled over a communication network. In some embodiments, the apparatus 200 may be electrically powered. In some embodiments, the apparatus 200 may include a storage device 208 configured for storing data. Further, in some embodiments, the apparatus 200 may include a processing device 206 configured for performing at least one operation on the data. Further, in some embodiments, the apparatus 200 may include an output device including at least one of a display device and a sound production device. Further, in some embodiments, the apparatus 200 may be used by some personnel in a health care institution.

Figure 9:
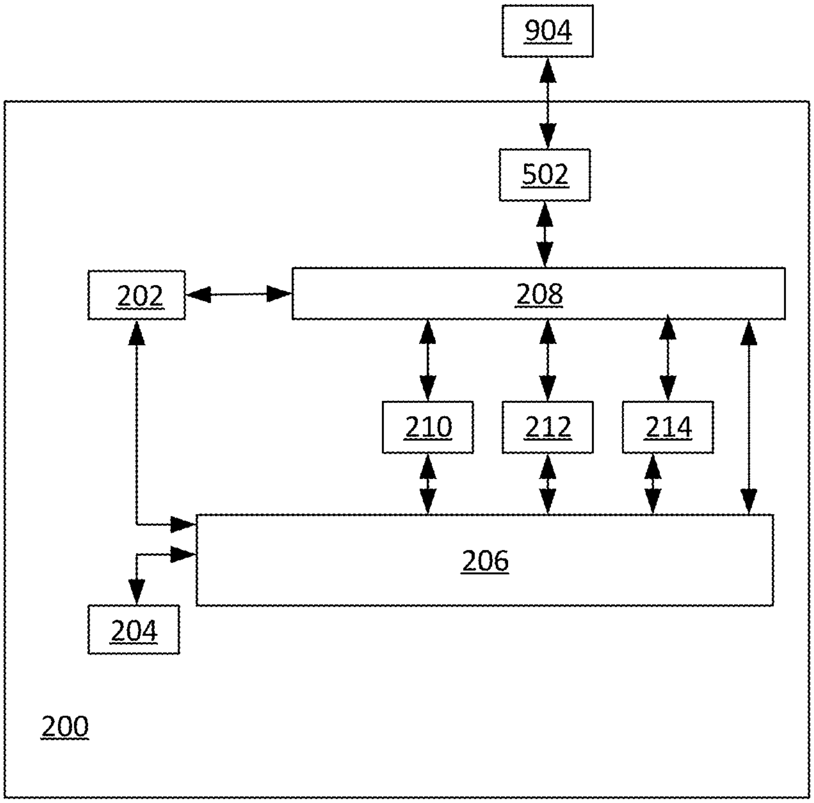
FIG. 9 is a block diagram of the apparatus 200 for facilitating presentation of medical data, in accordance with some embodiments.

Further, the apparatus 200 may include the storage device 208 configured for storing at least one medical data. Further, the at least one medical data may include, but not be limited to, data associated with one or more of a living and non-living state of mammals. In some embodiments, the at least one medical data may include, but not be limited to, a feature pertinent to health and wellness, a cause of mortality, and a cause of reproduction. In some embodiments, the at least one medical data may be used in healthcare institutions for decision-making, research, and provision of services. In some embodiments, the at least one medical data may include, but not be limited to, patient data and/or clinical data. In some embodiments, the at least one medical data includes, but is not limited to, diagnostic images, x-ray images, videos of surgical procedures, and patient vitals. Further, the storage device 208 may be configured to read and write at least one data. In some embodiments, the storage device 208 may include a disk with a magnetic coating, wherein the disk may be a hard disk drive, a solid-state drive, etc. In another embodiment, the storage device 208 may be coupled with a communication device 502, as shown in FIG. 9, to receive the at least one medical data.

Further, the apparatus 200 may include the processing device 206 communicatively coupled with at least one of the microphone 202 and the hand tracking device 204. Further, the processing device 206 may be configured for analyzing at least one of the sound data and the gesture data. Further, the processing device 206 may be configured for generating an instruction based on the analyzing. Further, the processing device 206 may be configured for performing at least one operation on the at least one medical data based on the instruction. Further, the at least one operation may include at least one of causing presenting of the at least one medical data and manipulating of the at least one medical data on at least one of a head-mountable device 210, an ophthalmic device 212, and an implantable device 214. Further, the microphone 202 may be a device that is configured to detect a sound vibration in a medium and convert the sound vibration into an electronic signal. In some embodiments, the microphone 202 may include a diaphragm, wherein a vibrating of the diaphragm creates the sound vibration. In some embodiments, the microphone 202 may be electrically powered. In some embodiments, the microphone 202 may be configured to detect an utterance from a user. Further, the hand-tracking-device 204 may include any device configured to track a hand of a user. In some embodiments, the hand-tracking-device 204 may include a sensor configured to track the hand. In some embodiments, the sensor may be affixed to a part of a hand of a user. In some embodiments, the hand-tracking device 204 may be configured to detect a hand gesture of the user. In some embodiments, the hand-tracking device 204 may be configured to be used by personnel in a healthcare institution. In some embodiments, the hand-tracking device 204 may include at least one receptacle configured to receive at least one part of the hand. For example, the at least one receptacle may include a plurality of receptacles configured to receive a plurality of fingers of the hand. In some embodiments, the hand-tracking device 204 may include a hand-glove. In some embodiments, the hand-tracking device 204 may include a motion-tracking glove. Further, the sound data may be representative of a sound wave. In some embodiments, the sound data may include a representation of a frequency and an amplitude of the sound wave. In some embodiments, the sound data may include a representation of a raw or a processed form of the sound wave. In some embodiments, the sound data may be a data generated by providing input to the microphone 202. In some embodiments, the sound data may be transmitted to a recording medium or/and a presentation device. In some embodiments, the sound data may include one or more utterance of the user in a form of an electrical signal. In some embodiments, the sound data may be analyzed by the processing device 206 for speech training of the one or more utterances of the user. Further, the gesture data may be representative of a movement of at least one bodily part of a user. For example, the at least one bodily part may be of a hand, an arm, or a wrist of the user. In an embodiment, gesture data is generated by providing input to a hand-tracking device 204. In some embodiments, the gesture data may also include a foot gesture data, a head gesture data, or an eye gesture data.

Further, the apparatus 200 may include at least one of the head-mountable device 210, the ophthalmic device 212, and the implantable device 214 communicatively coupled with each of the processing device 206 and the storage device 208. Further, each of the head-mountable device 210, the ophthalmic device 212, and the implantable device 214 may include at least one of a display device and a sound production device. Further, at least one of the head-mountable device 210, the ophthalmic device 212, and the implantable device 214 may be configured for presenting the at least one medical data based on the performing of the at least one operation. Further, the display device is an output device configured to present at least one medical data in one or more of a visual or a tactile form. In an embodiment, the display device is a component of a presentation device. In some embodiments, the display device may obtain at least one medical data from a communication device. In some embodiments, the display device may be coupled with the sound production device. In some embodiments, the display device may include a monitor, a screen, an LED, etc. Further, the sound production device is configured to create a sound by generating a waveform. In an embodiment, the sound production device is a component of the presentation device. In some embodiments, the sound production device may include a speaker, wherein a user perceives the sound created by the waveform. In some embodiments, the sound production device may include a diaphragm, wherein a vibrating of the diaphragm creates the sound. Further, the head-mountable device 210 comprises the display device and the sound production device. In an embodiment, the head-mountable device 210 may include a device worn on a head or as a part of a helmet. In some embodiments, the head-mountable device 210 may include a display optic in front of an eye of the user. In some embodiments, the head-mountable device 210 may be integrated into a goggle, a headset, a hat, etc. In some embodiments, the head-mountable device 210 may present the at least one medical data in a mixed-reality environment. In some embodiments, the head-mountable device 210 may be used by personnel in a healthcare institution. Further, the ophthalmic device 212 may include a display optic in front of an eye of a user. In some embodiments, the ophthalmic device 212 may be used in ophthalmology and optometry. In some embodiments, the ophthalmic device 212 may be coupled with the sound production device. In some embodiments, the ophthalmic device 212 may present the at least one medical data in a mixed-reality environment. In some embodiments, the ophthalmic device 212 may be used by ophthalmologists for diagnosing the at least one medical data associated with vision. Further, the implantable device 214 may include a device that is usually wholly or partially introduced into a body of the user. In some embodiments, the implantable device 214 may include an intraocular implant comprising an artificial lens placed inside an eye of the user. Accordingly, in some embodiments, the artificial lens may be configured to receive light from the display device. In some embodiments, the artificial lens may be configured to receive each of light from the display device and light from a real-world surrounding of the user. In some embodiments, the intraocular implant may include the display device comprising a light director configured to direct light corresponding to a display onto the retina of the eye. Further, the display device may be configured to pass through light (i.e. exhibiting transparency to visible light) from a real-world surrounding of the user. Accordingly, the intraocular implant may facilitate provisioning a mixed-reality experience. In some embodiments, the implantable device 214 may be coupled with the sound production device. In some embodiments, the intraocular implant may be configured to correct a visual defect of the eye of the user.

Further, in some embodiments, the apparatus 200 may be a wearable device.

Further, in some embodiments, the apparatus 200 may be an extended reality device. Further, the extended reality device may include a device operating on at least one of augmented reality (AR), virtual reality (VR), and mixed reality (MR) technologies. In some embodiments, the extended reality device is any device that presents the at least one medical data. In some embodiments, the extended reality device generally refers to the head-mountable device 210 comprising a sound production device and a display device. In some embodiments, the extended reality device is used by a surgeon during surgical procedures.

Figure 3:
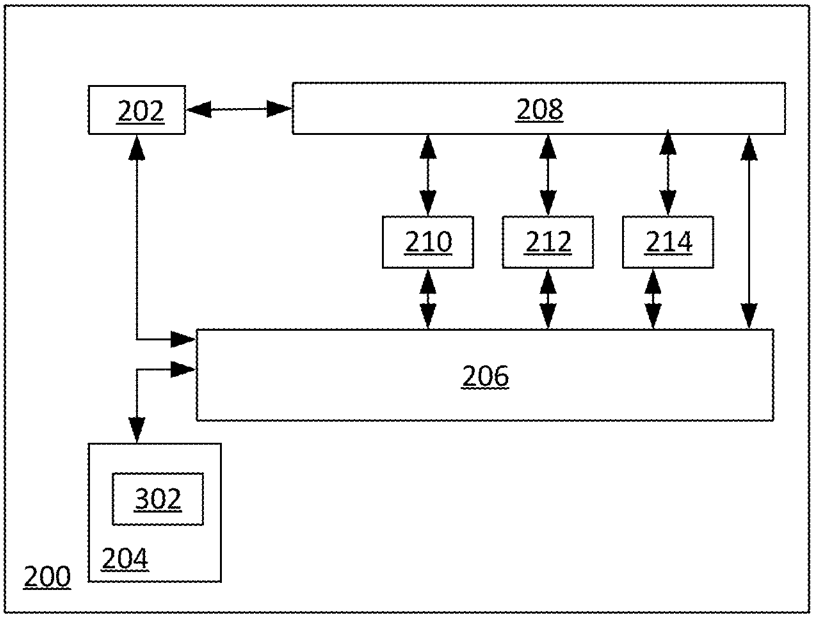
FIG. 3 is a block diagram of the apparatus 200 for facilitating presentation of medical data, in accordance with some embodiments.

Further, in some embodiments, the hand tracking device 204 may include a motion tracking glove 302, as shown in FIG. 3, configured for generating the gesture data by tracking the hand gesture of a user associated with the apparatus 200.

Figure 4:
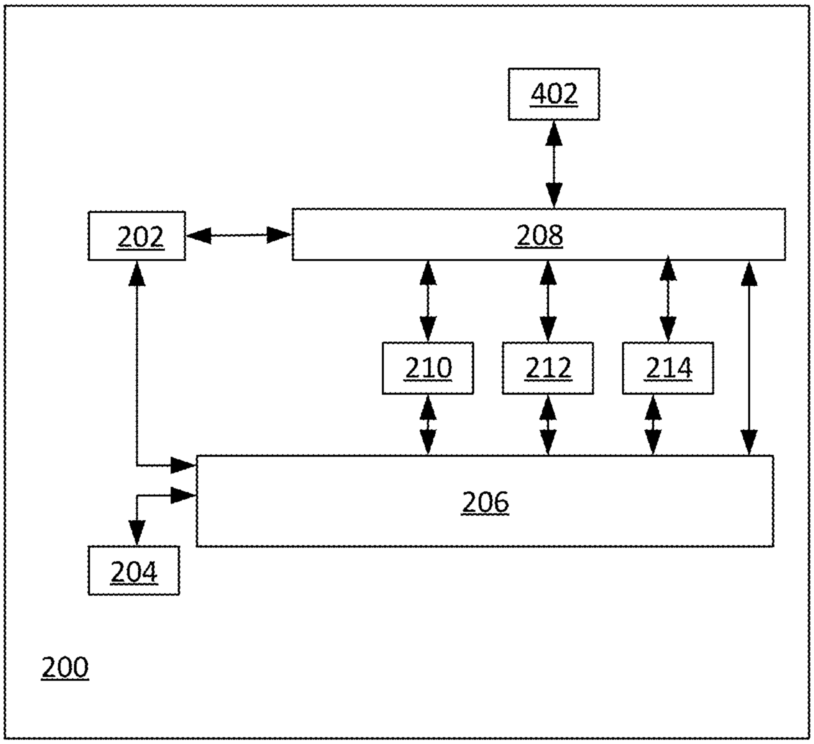
FIG. 4 is a block diagram of the apparatus 200 for facilitating presentation of medical data, in accordance with some embodiments.

Further, in some embodiments, the apparatus 200 further may include an image sensor 402, as shown in FIG. 4, communicatively coupled with the storage device 208. Further, the image sensor 402 may be configured for generating one or more image data. Further, the processing device 206 may be further configured for analyzing the one or more image data. Further, the generating of the instruction may be further based on the analyzing of the one or more image data.

Further, in an embodiment, the at least one operation further may include causing storing of the one or more image data.

Further, in some embodiments, the at least one of the head-mountable device 210, the ophthalmic device 212, and the implantable device 214 may include a heads-up display screen. Further, the at least one operation further may include at least one of a repositioning and a resizing of the heads-up display screen.

Further, in some embodiments, the at least one of the head-mountable device 210, the ophthalmic device 212, and the implantable device 214 may include a heads-up display screen. Further, the at least one operation further may include at least one of causing selecting of at least one of a screen type and a screen input associated with the heads-up display screen and creating one or more options of a menu for the heads-up display screen.

Further, in an embodiment, the at least one operation further may include creating a custom path for the one or more options of the menu.

Further, in an embodiment, the at least one operation further may include at least one of causing displaying and navigating between the one or more options of the menu.

Further, in an embodiment, the at least one operation further may include at least one of causing overlaying a first menu over a second menu on the heads-up display screen.

Figure 6:
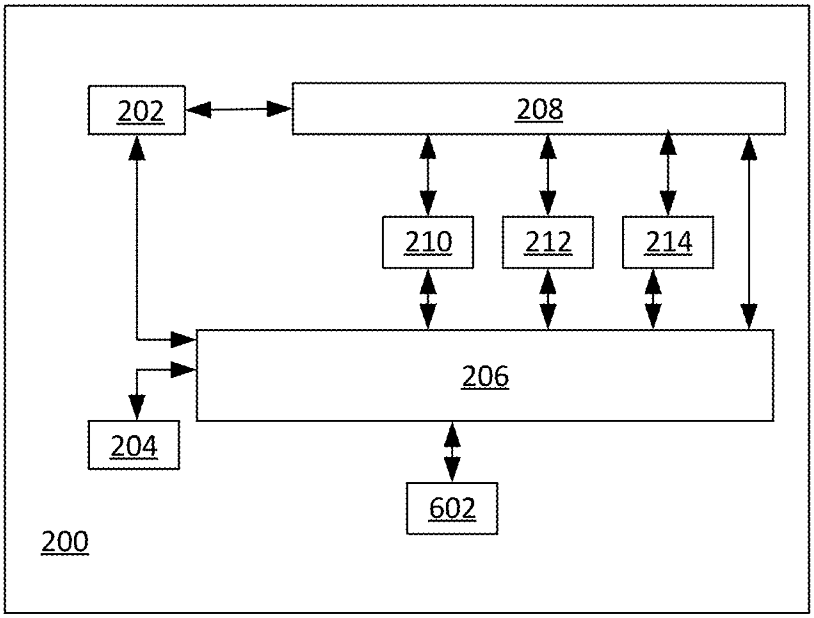
FIG. 6 is a block diagram of the apparatus 200 for facilitating presentation of medical data, in accordance with some embodiments.

Further, in some embodiments, the apparatus 200 further may include a footswitch 602, as shown in FIG. 6, configured for generating a foot gesture data representing one or more foot gestures of the user. Further, the footswitch 602 may be communicatively coupled with the processing device 206. Further, the processing device 206 may be further configured for analyzing the foot gesture data. Further, the generating of the instruction may be further based on the analyzing of the foot gesture data.

Figure 7:
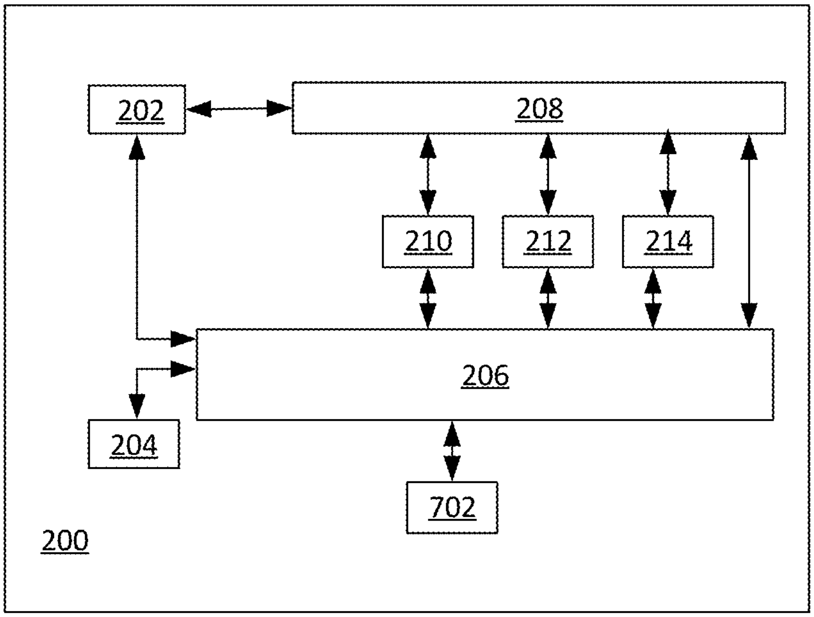
FIG. 7 is a block diagram of the apparatus 200 for facilitating presentation of medical data, in accordance with some embodiments.

Further, in some embodiments, the apparatus 200 further may include a head tracking device 702, as shown in FIG. 7, configured for generating a head gesture data representing one or more head gestures of the user. Further, the head tracking device 702 may be communicatively coupled with the processing device 206. Further, the processing device 206 may be further configured for analyzing the head gesture data. Further, the generating of the instruction may be further based on the analyzing of the head gesture data.

Figure 8:
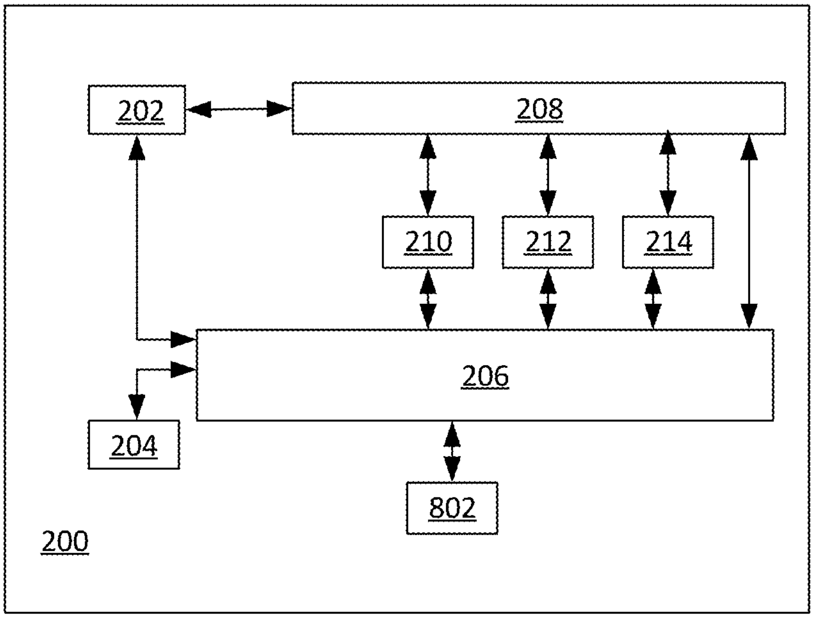
FIG. 8 is a block diagram of the apparatus 200 for facilitating presentation of medical data, in accordance with some embodiments.

Further, in some embodiments, the apparatus 200 further may include an eye tracking device 802, as shown in FIG. 8, configured for generating an eye gesture data representing one or more eye gestures of the user. Further, the eye tracking device 802 may be communicatively coupled with the processing device 206. Further, the processing device 206 may be further configured for analyzing the eye gesture data. Further, the generating of the instruction may be further based on the analyzing of the eye gesture data.

Figure 5:
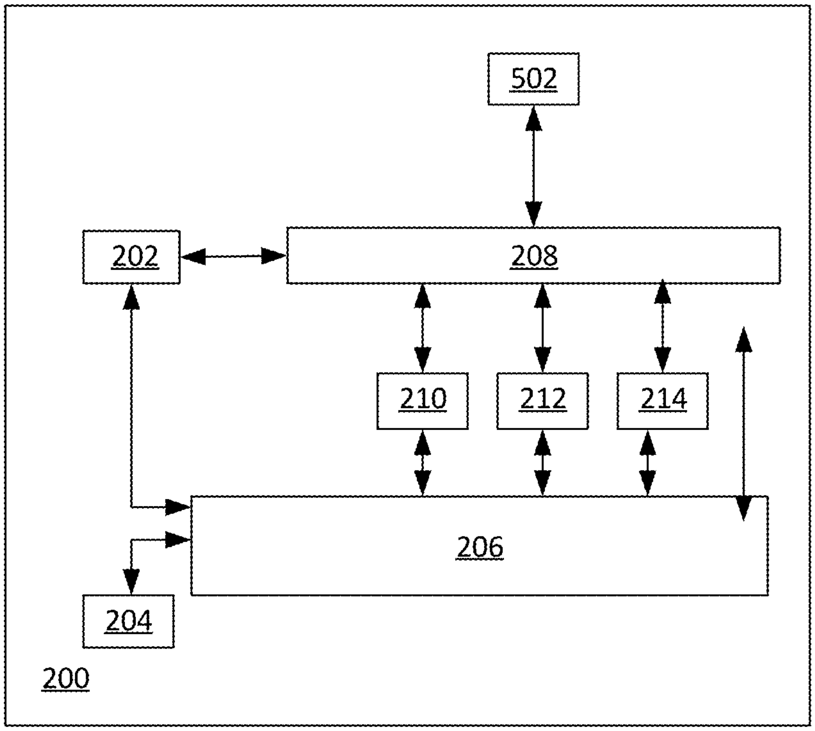
FIG. 5 is a block diagram of the apparatus 200 for facilitating presentation of medical data, in accordance with some embodiments.

Further, in some embodiments, the apparatus 200 further may include a communication device 502, as shown in FIG. 5, configured for receiving the at least one medical data from an external medical system 904, as shown in FIG. 9. Further, the communication device 502 may be communicatively coupled with the storage device 208.

Figure 10:
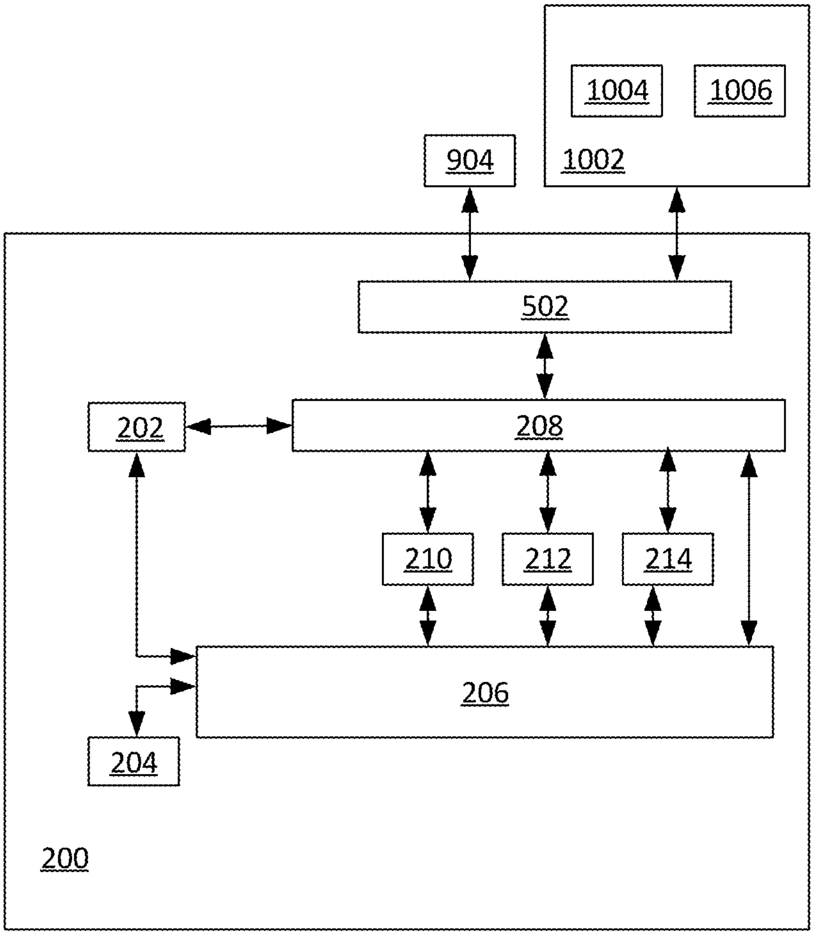
FIG. 10 is a block diagram of the apparatus 200 for facilitating presentation of medical data, in accordance with some embodiments.

Further, in an embodiment, the communication device 502 may be further configured for transmitting the at least one medical data to a secondary presentation device 1002, as shown in FIG. 10. Further, the secondary presentation device 1002 may include at least one of a secondary display device 1004 and a secondary sound production device 1006.

Figure 11:
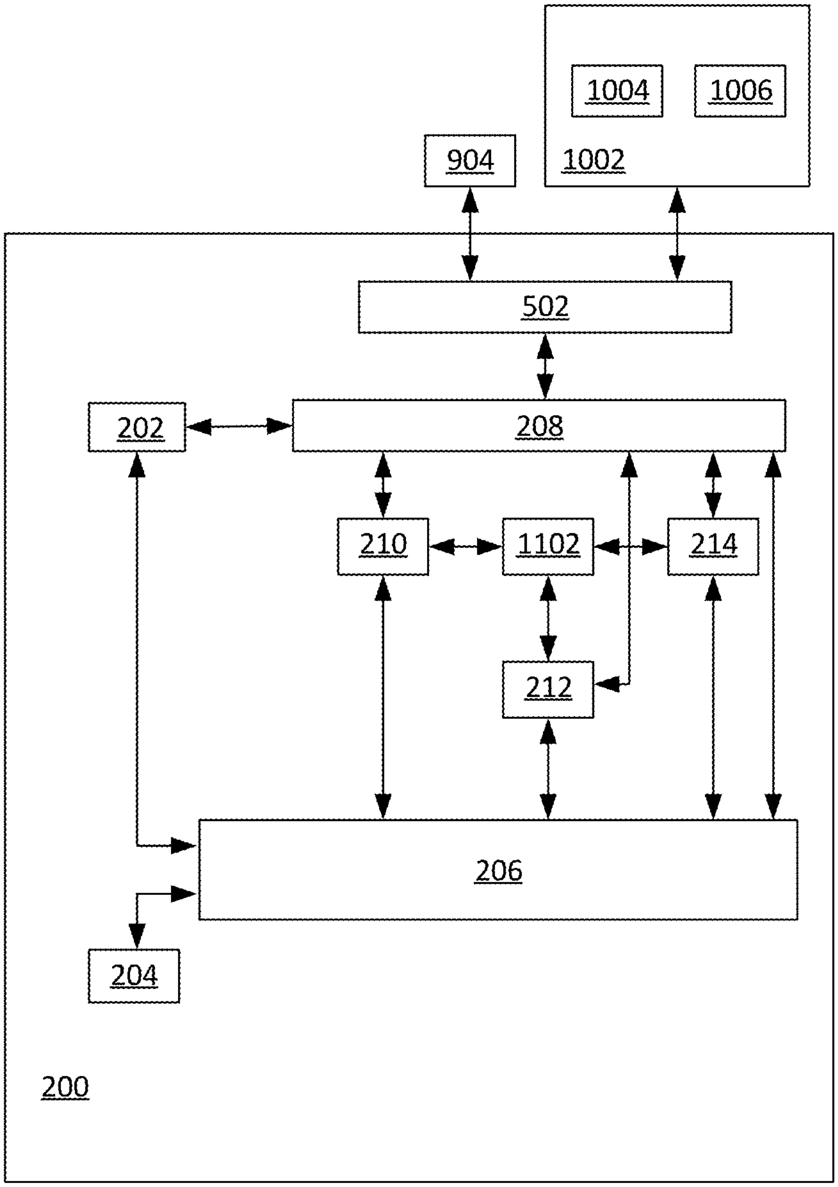
FIG. 11 is a block diagram of the apparatus 200 for facilitating presentation of medical data, in accordance with some embodiments.

Further, in an embodiment, the apparatus 200 further may include a proximity sensor 1102, as shown in FIG. 11, communicatively coupled with at least one of the head-mountable device 210, the ophthalmic device 212, and the implantable device 214. Further, the proximity sensor 1102 may be configured for detecting a presence of the secondary presentation device 1002 may include at least one of the display device 1004 and the sound production device 1006 in a vicinity of the apparatus 200. Further, the transmitting of the at least one medical data may be based on the detecting of the presence of the secondary presentation device 1002.

Further, in some embodiments, the at least one operation further may include cropping a first medical data of the at least one medical data. Further, the at least one operation further may include at least one of repositioning and resizing the first medical data based on the cropping. Further, the at least one operation further may include overlaying of the first medical data over a second medical data of the at least one medical data presented on the at least one of the head-mountable device 210, the ophthalmic device 212, the implantable device 214, and the secondary presentation device 1002 based on at least one of the repositioning and the resizing.

Further, in some embodiments, the analyzing of the at least one of the sound data and the gesture data may be based on a machine learning model.

FIG. 3 is a block diagram of the apparatus 200 for facilitating presentation of medical data, in accordance with some embodiments.

FIG. 4 is a block diagram of the apparatus 200 for facilitating presentation of medical data, in accordance with some embodiments.

FIG. 5 is a block diagram of the apparatus 200 for facilitating presentation of medical data, in accordance with some embodiments.

FIG. 6 is a block diagram of the apparatus 200 for facilitating presentation of medical data, in accordance with some embodiments.

FIG. 7 is a block diagram of the apparatus 200 for facilitating presentation of medical data, in accordance with some embodiments.

FIG. 8 is a block diagram of the apparatus 200 for facilitating presentation of medical data, in accordance with some embodiments.

FIG. 9 is a block diagram of the apparatus 200 for facilitating presentation of medical data, in accordance with some embodiments.

FIG. 10 is a block diagram of the apparatus 200 for facilitating presentation of medical data, in accordance with some embodiments.

FIG. 11 is a block diagram of the apparatus 200 for facilitating presentation of medical data, in accordance with some embodiments.

Figure 12:
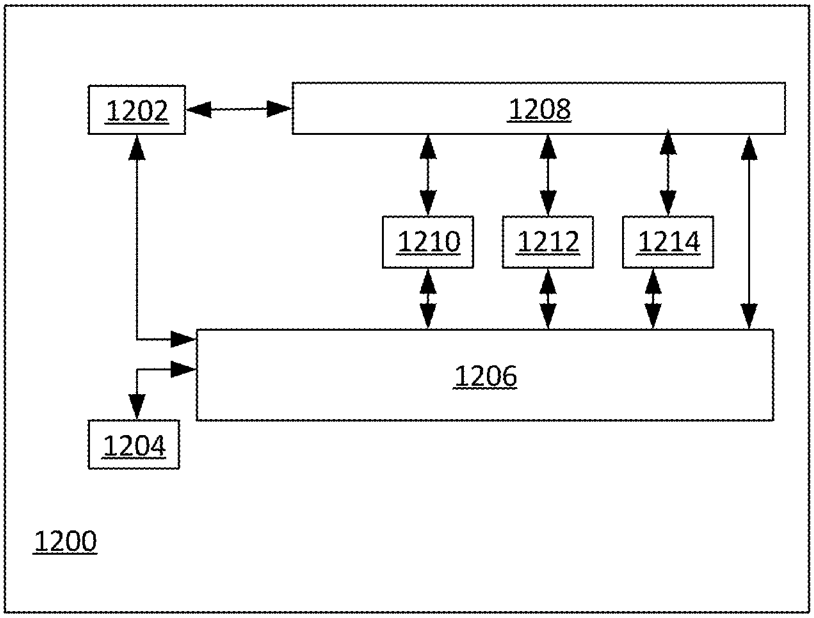
FIG. 12 is a block diagram of an apparatus 1200 for facilitating presentation of medical data, in accordance with some embodiments.

FIG. 12 is a block diagram of an apparatus 1200 for facilitating presentation of medical data, in accordance with some embodiments. Accordingly, the apparatus 1200 may include at least one of a microphone 1202 and a hand tracking device 1204. Further, the microphone 1202 may be configured for generating a sound data and the hand tracking device 1204 may be configured for generating a gesture data based on a hand gesture. Further, the hand tracking device 1204 may include a motion tracking glove configured for generating the gesture data by tracking the hand gesture of a user associated with the apparatus 1200. Further, the microphone 1202 may be configured for generating a sound data and the hand tracking device 1202 may be configured for generating a gesture data based on a hand gesture. Further, used herein, the apparatus 1200 may include a combination of one or more tangible devices configured to co-operate with each other to perform one or more functions. In some embodiments, the apparatus 1200 may include a network of devices communicatively coupled over a communication network. In some embodiments, the apparatus 1200 may be electrically powered. In some embodiments, the apparatus 1200 may include a storage device 1208 configured for storing data. Further, in some embodiments, the apparatus 1200 may include a processing device 1206 configured for performing at least one operation on the data. Further, in some embodiments, the apparatus 1200 may include an output device including at least one of a display device and a sound production device. Further, in some embodiments, the apparatus 1200 may be used by personnel in a health care institution.

Further, the apparatus 1200 may include the storage device 1208 configured for storing at least one medical data. Further, the at least one medical data may include data associated with one or more of a living and non-living state of mammals. In some embodiments, the at least one medical data may include a feature pertinent to health and wellness, a cause of mortality, and a cause of reproduction. In some embodiments, the at least one medical data may be used in healthcare institutions for decision-making, research, and provision of services. In some embodiments, the at least one medical data may include patient data and/or clinical data. In some embodiments, the at least one medical data includes diagnostic images, x-ray images, videos of surgical procedures, and patient vitals. Further, the storage device 1208 may be configured to read and write at least one data. In some embodiments, the storage device 1208 may include a disk with a magnetic coating, wherein the disk may be a hard disk drive, a solid-state drive, etc. In another embodiment, the storage device 1208 may be coupled with a communication device to receive the at least one medical data.

Further, the apparatus 1200 may include the processing device 1206 communicatively coupled with at least one of the microphone 1202 and the hand tracking device 1204. Further, the processing device 1206 may be configured for analyzing at least one of the sound data and the gesture data. Further, the processing device 1206 may be configured for generating an instruction based on the analyzing. Further, the processing device 1206 may be configured for performing at least one operation on the at least one medical data based on the instruction. Further, the at least one operation may include at least one of causing presenting of the at least one medical data and manipulating of the at least one medical data on at least one of a head-mountable device 1210, an ophthalmic device 1212, and an implantable device 1214.

Further, the apparatus 1200 may include at least one of the head-mountable device 1210, the ophthalmic device 1212, and the implantable device 1214 communicatively coupled with each of the processing device 1206 and the storage device 1208. Further, each of the head-mountable device 1210, the ophthalmic device 1212, and the implantable device 1214 may include at least one of a display device and a sound production device. Further, at least one of the head-mountable device 1210, the ophthalmic device 1212, and the implantable device 1214 may be configured for presenting the at least one medical data based on the performing of the at least one operation. Further, the display device is an output device configured to present at least one medical data in one or more of a visual or a tactile form. In an embodiment, the display device is a component of a presentation device. In some embodiments, the display device may obtain at least one medical data from a communication device. In some embodiments, the display device may be coupled with the sound production device. In some embodiments, the display device may include a monitor, a screen, an LED, etc. Further, the sound production device is configured to create a sound by generating a waveform. In an embodiment, the sound production device is a component of the presentation device. In some embodiments, the sound production device may include a speaker, wherein a user perceives the sound created by the waveform. In some embodiments, the sound production device may include a diaphragm, wherein a vibrating of the diaphragm creates the sound. Further, the head-mountable device 1210 comprises the display device and the sound production device. In an embodiment, the head-mountable device 1210 may include a device worn on a head or as a part of a helmet. In some embodiments, the head-mountable device 1210 may include a display optic in front of an eye of the user. In some embodiments, the head-mountable device 1210 may be integrated into a goggle, a headset, a hat, etc. In some embodiments, the head-mountable device 1210 may present the at least one medical data in a mixed-reality environment. In some embodiments, the head-mountable device 1210 may be used by personnel in a healthcare institution. Further, the ophthalmic device 1212 may include a display optic in front of an eye of a user. In some embodiments, the ophthalmic device 1212 may be used in ophthalmology and optometry. In some embodiments, the ophthalmic device 1212 may be coupled with the sound production device. In some embodiments, the ophthalmic device 1212 may present the at least one medical data in a mixed-reality environment. In some embodiments, the ophthalmic device 1212 may be used by ophthalmologists for diagnosing the at least one medical data associated with vision. Further, the implantable device 1214 may include a device that is usually wholly or partially introduced into a body of the user. In some embodiments, the implantable device 1214 may include an intraocular implant comprising an artificial lens placed inside an eye of the user. Accordingly, in some embodiments, the artificial lens may be configured to receive light from the display device. In some embodiments, the artificial lens may be configured to receive each of light from the display device and light from a real-world surrounding of the user. In some embodiments, the intraocular implant may include the display device comprising a light director configured to direct light corresponding to a display onto the retina of the eye. Further, the display device may be configured to pass through light (i.e. exhibiting transparency to visible light) from a real-world surrounding of the user. Accordingly, the intraocular implant may facilitate provisioning a mixed-reality experience. In some embodiments, the implantable device 1214 may be coupled with the sound production device. In some embodiments, the intraocular implant may be configured to correct a visual defect of the eye of the user.

Figure 13:
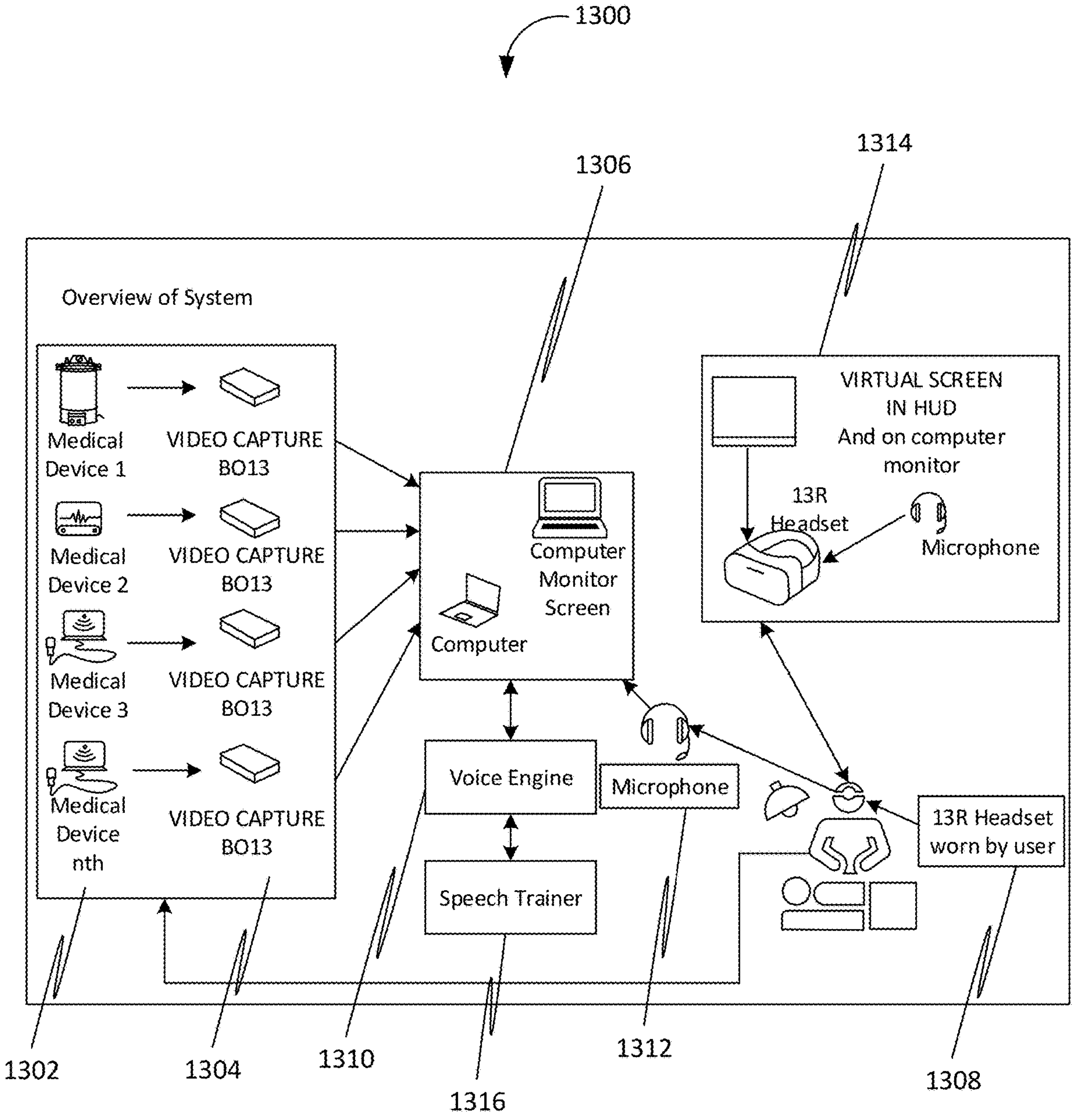
FIG. 13 is a schematic of an apparatus 1300 designed to facilitate the manipulation of multiple data displays shown in a display device based on user commands, in accordance with some embodiments.

FIG. 13 is a schematic of an apparatus 1300 designed to facilitate the manipulation of multiple data displays shown in a display device based on user commands, in accordance with some embodiments. Accordingly, the system may include at least one medical device 1302 (data output source), at least one video capture device 1304 a computer 1306 coupled to a head mounted display 1308, the head mounted display 1308 configured to be worn by the user a voice engine UI 1310 with training component 1316 installed on the computer 1306 configured to respond to and record the users voice commands received by the computer 1306, a microphone 1312 to pick up voice commands from the user and a user interface 1314 comprising at least: the head mounted display, and multiple video inputs, and configured to provide to the computer a voice input received from the headset in association with a virtual hand motion input received from the hand tracking device 1204, to manipulate in the first system mode the screen size, type, and position; and perform in the second system mode action of relaying to the computer the actions initiated by the user's voice commands to take a photo or short video from an input device. In further embodiments, disclosed herein is a method for interacting with a head-mounted display system 1308, wherein the method comprising displaying, to a user, an image relating to a medical procedure on a head-mounted display 1308, receiving a voice command input by the user from the microphone 1312 in association to the displayed image, and applying the voice command input received to perform an action on the image in a head-up display (HUD) device.

Figure 14:
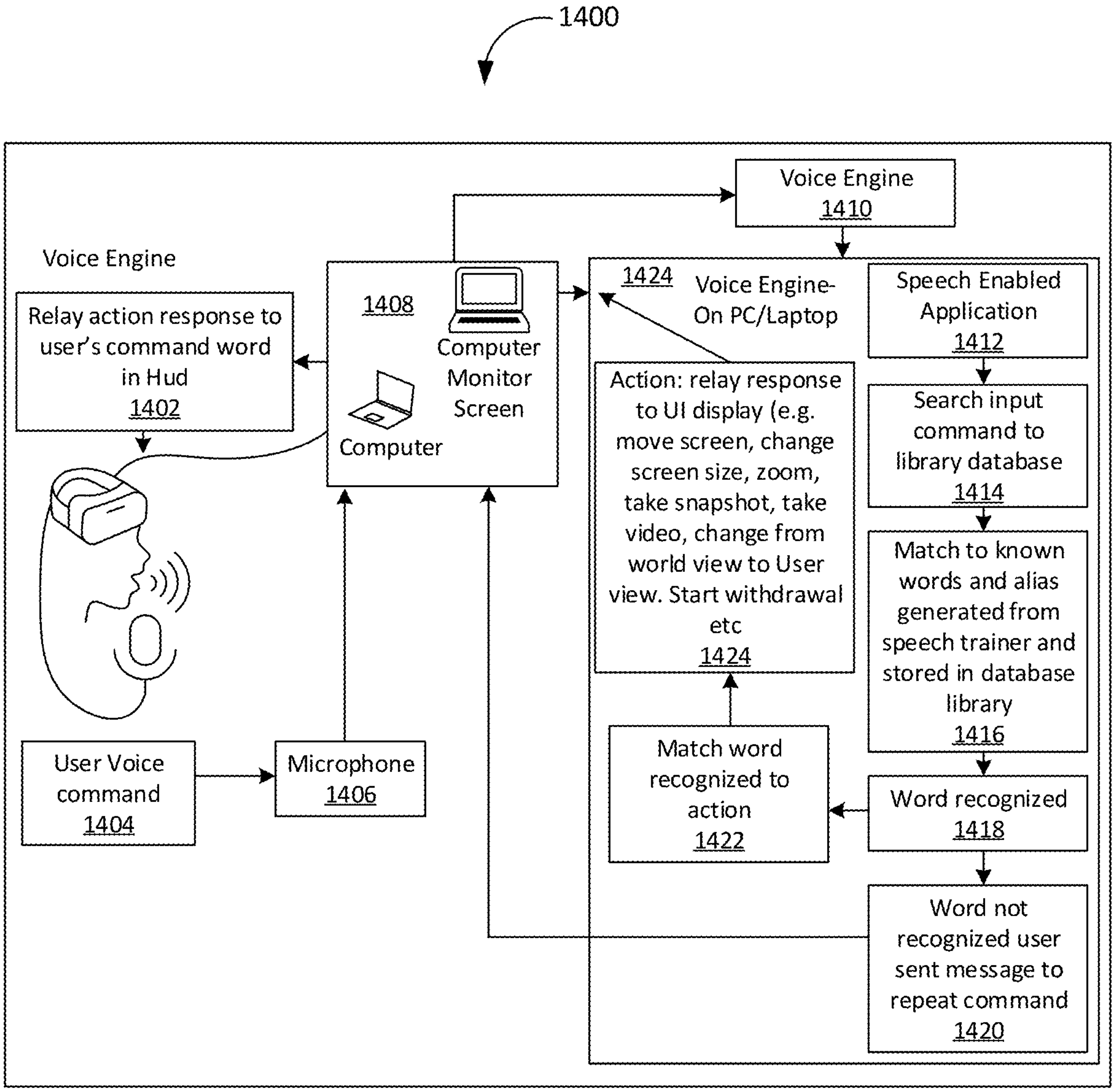
FIG. 14 is a schematic of a method 1400 designed to facilitate the manipulation of multiple data displays shown in a display device based on user commands using a voice engine, in accordance with some embodiments.

FIG. 14 is a schematic of a method 1400 designed to facilitate the manipulation of multiple data displays shown in a display device based on user commands using a voice engine, in accordance with some embodiments. Accordingly, the method 1400 may include using a customizable voice engine with an integrated voice training system to create new menu options in the HUD and on the computer monitor display. Further, the voice engine system may be used to create a custom path of menu choices for a user to interactively navigate a user through a path of menu choices using voice commands on a virtual or real user interface to lead the user through a computer application. Such a method is performed automatically by at least one hardware processor. The method 1400, in an embodiment, may include displaying a current menu of choices in the first area of a user interface display. The method 1400 includes a selection of a first menu item choice that may auto-populate a second menu selection option based on the first menu item choice and displayed in the first area of a user interface display. The method 1400 may further include displaying a second area overlaid on the first virtual HUD or monitor's display screen initiated by a choice from the first menu. For instance, a first menu choice may initiate a timer to be displayed in an overlay on the first area image shown on the virtual or real screen. Another example is to take a snapshot of an area of the screen that may show for 1 second a message that a snapshot was taken in the HUD screen and the computer monitor screen. Further, at 1404 the method 1400 may include a user providing a voice command.

Further, at 1406 the method 1400 may include receiving the voice command using a microphone.

Further, at 1408 the method 1400 may include processing the voice command.

Further, at 1410 the method 1400 may include analyzing the voice command using a voice engine.

Further, at 1412 the method 1400 may include using speech enabled application.

Further, at 1414 the method 1400 may include searching input command to library database.

Further, at 1416 the method 1400 may include matching to known words and aliases generated from speech trainer and stored in a database library.

Further, at 1418 the method 1400 may include recognizing a word.

Further, at 1420 the method 1400 may include not recognizing the word and sent a message to the user to repeat the command.

Further, at 1422 the method 1400 may include matching word recognized to action.

Further, at 1422 the method 1400 may include providing a relay response to a user interface (UI) display (e.g. move screen, change screen size, zoom, take a snapshot, video, changing from world view to user view, Start withdrawal etc.).

Further, at 1402 the method 1400 may include sending a relay action response to user's command word in HUD.

Figure 15:
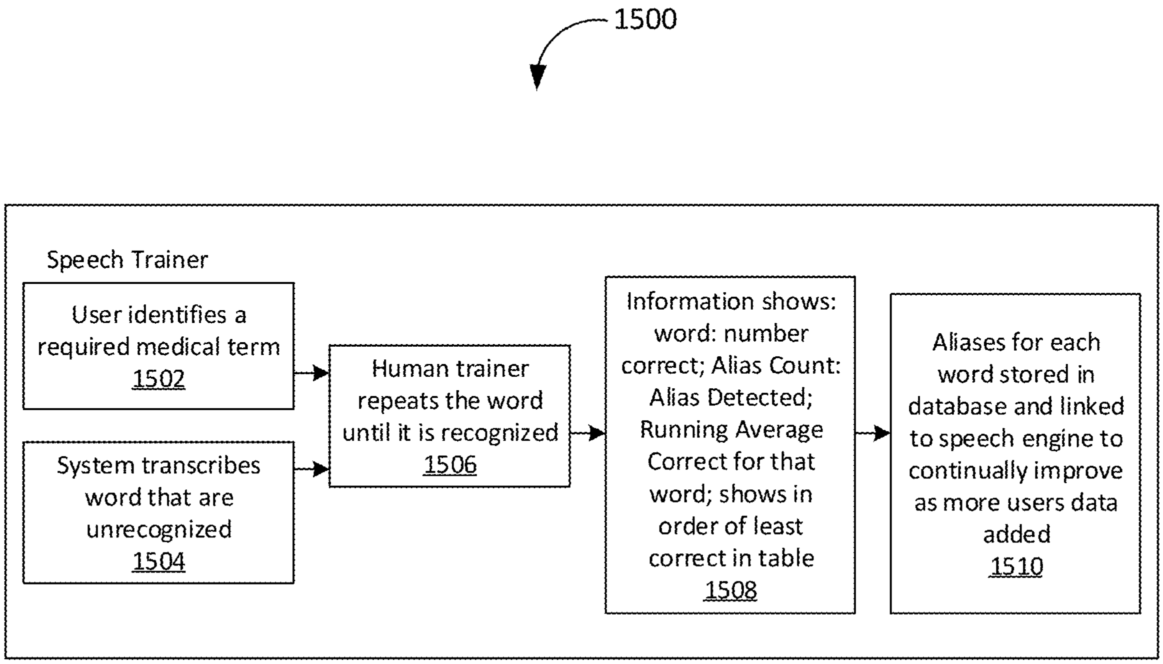
FIG. 15 is a flow diagram of a method 1500 for facilitating manipulation of multiple data displays shown in a display device based on user commands using a speech training system, in accordance with some embodiments.

FIG. 15 is a flow diagram of a method 1500 for facilitating manipulation of multiple data displays shown in a display device based on user commands using a speech training system, in accordance with some embodiments. Accordingly, the method 1500 includes using a speech training system. Further, the method may be performed automatically by at least one hardware processor. The method may include capturing the input option words created by the user and displayed in the option boxes on the flow chart of the voice engine creator and adding them to the voice trainer. The method, in the embodiment of the speech training, includes allowing a user to select from a menu item to add a new word to the speech trainer that is displayed on the first area of the user interface display. In an embodiment, the speech training system matches input words to a library of words or suggests aliases for the word. The word library and training results may be stored on a memory device operatively coupled to the hardware processor. The method, in this embodiment, may include displaying a current menu of aliases on a first portion of a user interface display and showing a running total of correct and alias attempts for each word. Further, at 1502 the method 1500 may include a user identifying a required medical term.

Further, at 1504 the method 1500 may include a system transcribing word that are unrecognized.

Further, at 1506 the method 1500 may include a human trainer repeating the word until it is recognized.

Further, at 1508 the method 1500 may include information showing: word, number correct, alias count, alias detected, running average correct for that word, shows in order of least correct in a table.

Further, at 1510 the method 1500 may include aliases for each word stored in a database and linked to a speech engine to continually improve as more user's data added.

Figure 16:
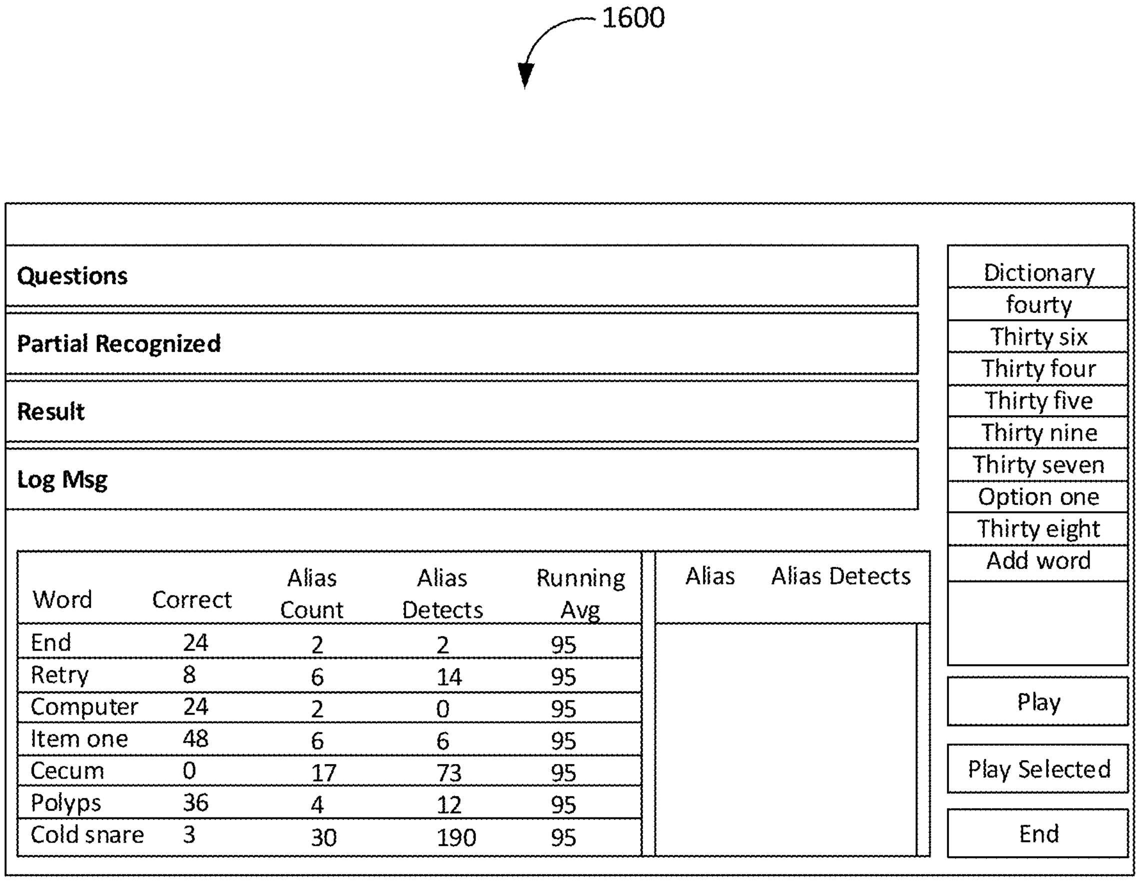
FIG. 16 is a screenshot of a user interface 1600 for facilitating manipulation of multiple data displays shown in a display device based on user commands using the speech training system, in accordance with some embodiments.

FIG. 16 is a screenshot of a user interface 1600 for facilitating manipulation of multiple data displays shown in a display device based on user commands using the speech training system, in accordance with some embodiments. Further, the user interface may be displayed on a presentation device such as a PC monitor, the HUD device, etc.

Figure 17:
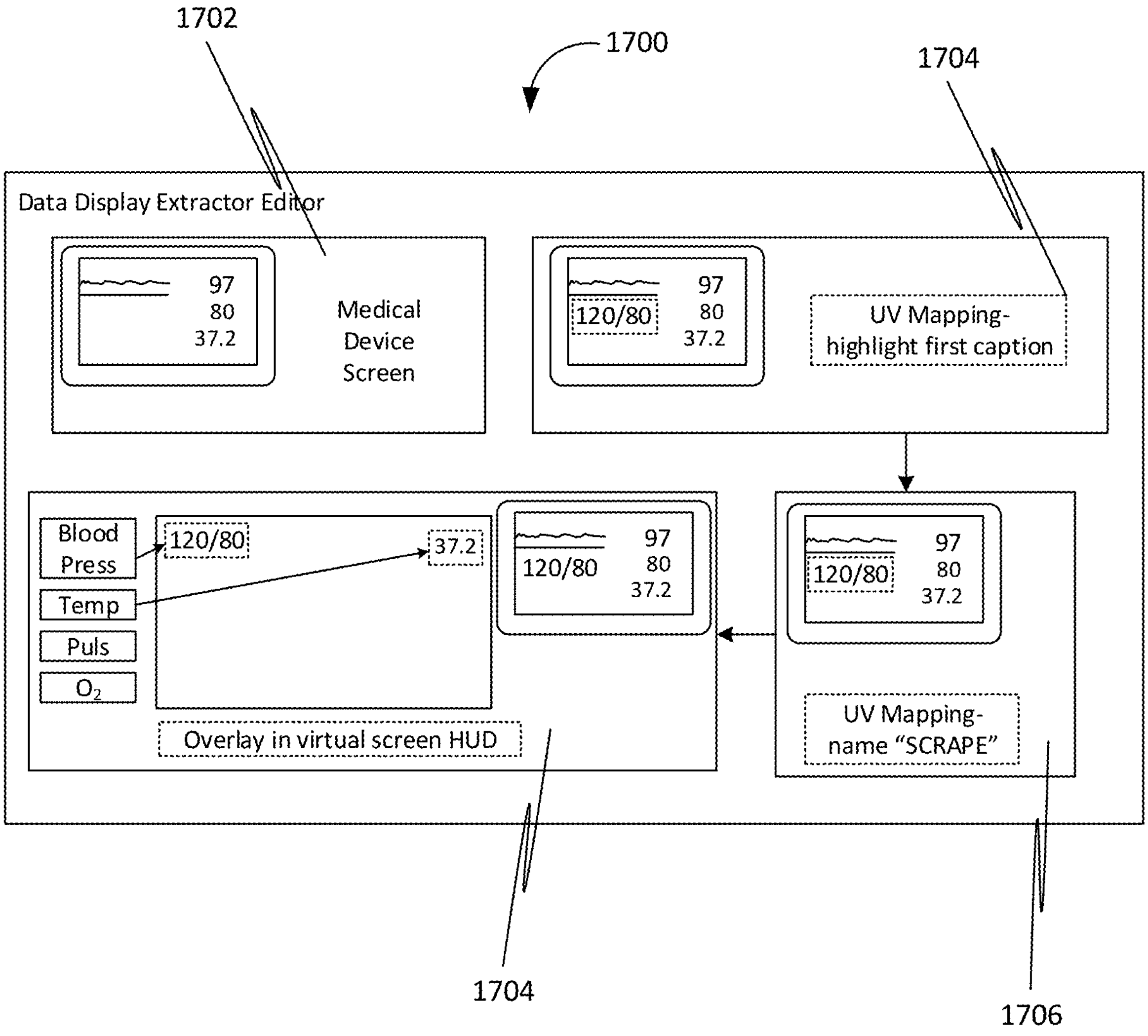
FIG. 17 is a flow diagram of a method 1700 for facilitating manipulation of multiple data displays shown in a display device based on user commands using a data display extraction editor, in accordance with some embodiments.

FIG. 17 is a flow diagram of a method 1700 for facilitating manipulation of multiple data displays shown in a display device based on user commands using a data display extraction editor, in accordance with some embodiments. Accordingly, the method 1700 at 1702 includes using the data display extraction editor. Further, the method 1700 at 1704 may include cropping specific parts of an image from a device's display screen and placing them on a virtual screen in customizable positions. Further, at 1706 the cropped image data in the virtual screen shown in the Heads Up Display (HUD) reflects the changing data on the device's display screen. The method, in the embodiment of the data display extraction editor, includes allowing a user to move the cropped sections using voice and/or virtual hands in the virtual monitor.

Further, at 1708, the method 1700 may include changing an interface of HUD.

Figure 18:
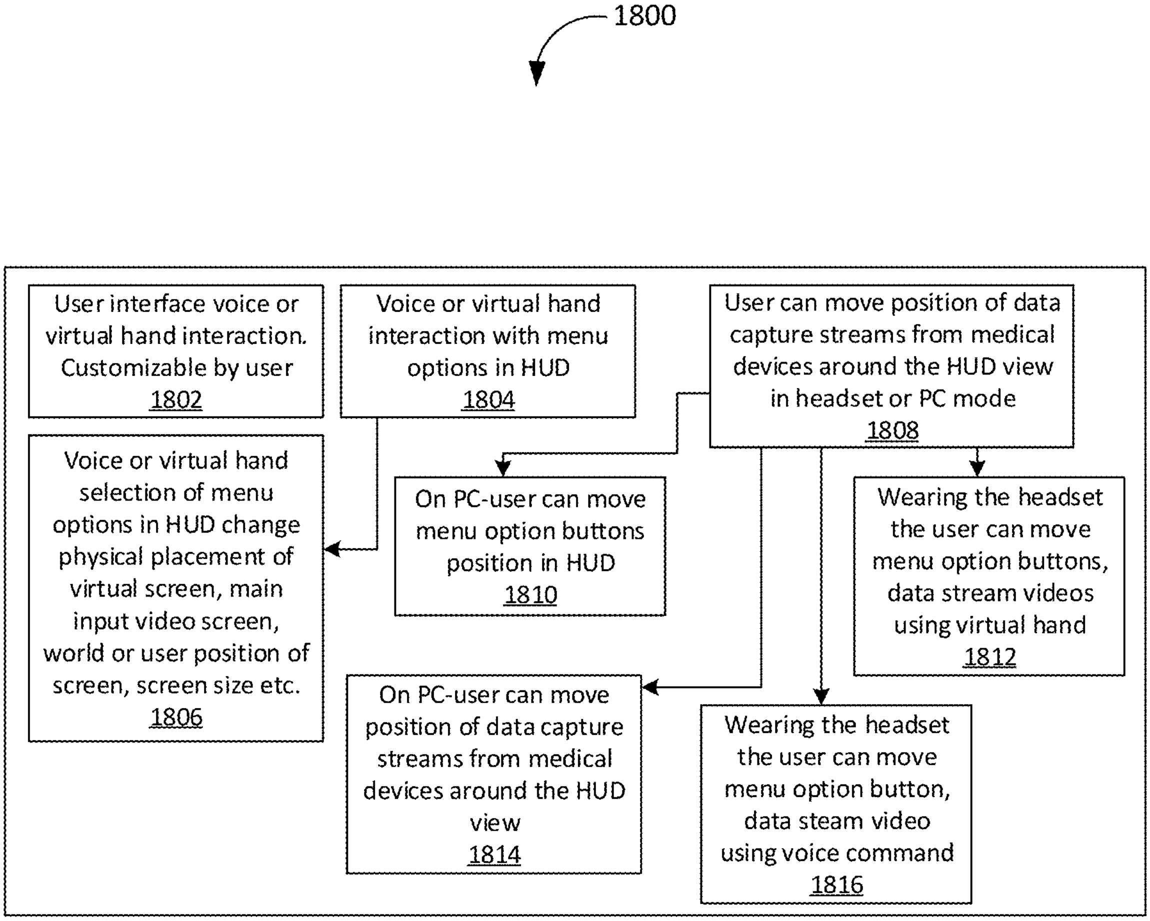
FIG. 18 is a flow diagram of a method 1800 for facilitating manipulation of multiple data displays shown in a display device based on user commands, in accordance with some embodiments.

FIG. 18 is a flow diagram of a method 1800 for facilitating manipulation of multiple data displays shown in a display device based on user commands, in accordance with some embodiments. Accordingly, the method includes generating, in a HUD (and/or on a computer monitor screen), a voice-activated menu of choices and displaying the current menu of choices in the first area of the user's virtual HUD (and the computer monitor screen). Further, the method is performed automatically by at least one hardware processor allows the user to voice select a menu item from a current menu of choices displayed in the first area of the UI virtual display (or in the computer monitor screen UI) and drill down through the menu level choices based on a selection of a menu choice from a prior level choice.

In some embodiments, the user interface further comprises a microphone configured to detect a voice command, wherein the input further comprises the voice command.

In some embodiments, the system may be further configured to display a menu overlaid on the image on the head-mounted display (and/or the computer monitor screen).

In some embodiments, controlling the properties of the image displayed via the HUD and the computer monitor screen by a voice action selected from the UI virtual (or real) menu may include selecting content of the image, zooming in and zooming out, scrolling between at least two virtual screens, displaying a picture in picture (PIP), displaying an overlay on a live image, centering the image, displaying a menu, navigating a menu, and controlling a region of interest of the image.

In some embodiments, the voice engine may be integrated with the head-mounted display (and the computer monitor screen) and is configured to change the size, position, and world position of the head-mounted display.

In some embodiments, the hand tracker may be integrated with the head-mounted display virtual buttons (and the computer monitor screen) and is configured to change the size, position, and world position of the head-mounted display.

In some embodiments, the system allows the clinician to use voice to command the system to take a photograph and/or video from a video feed and store it on the computer.

In some embodiments, the image of the medical field may be displayed via the head-mounted display in a display-stabilized state when the head-mounted display system is in the world position system mode, and wherein the video of the medical field is displayed via the head-mounted display in one of the multiple virtual screens in a world stabilized state.

In some embodiments, the computer is further configured to apply the voice command input to switch from the world position system HUD mode to the user-locked system HUD mode.

Further, at 1802 the method 1800 may include User interface voice or virtual hand interaction, customizable by a user.

Further, at 1804 the method 1800 may include voice or virtual hand interaction with menu options in HUD.

Further, at 1806 the method 1800 may include voice or virtual hand selection of menu options in HUD changing a physical placement of a virtual screen, main input video screen, world or user position of the screen, screen size, etc.

Further, at 1808 the method 1800 may include the user moving the position of data capture streams from medical devices around the HUD view in a headset or PC mode.

Further, at 1810 the method 1800 may include the user moving menu option buttons position in HUD on a personal computer (PC).

Further, at 1812 the method 1800 may include wearing the headset the user moving menu option buttons, data stream videos using virtual hand.

Further, at 1814 the method 1800 may include wearing the headset the user moving menu option button and data steam video using voice command.

Figure 19:
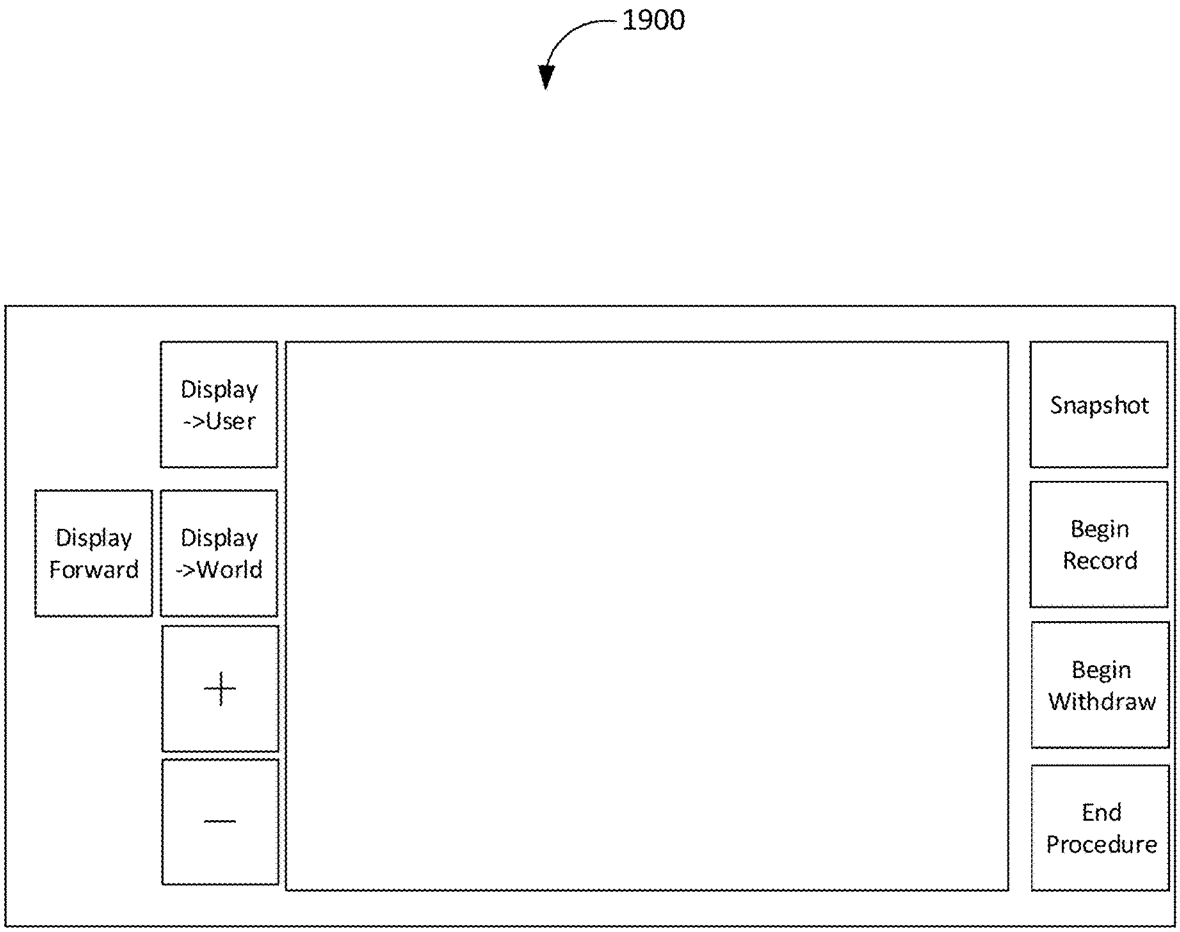
FIG. 19 is a screenshot of a user interface 1900 for facilitating manipulation of multiple data displays shown in a display device based on user commands, in accordance with some embodiments.

FIG. 19 is a screenshot of a user interface 1900 for facilitating manipulation of multiple data displays shown in a display device based on user commands, in accordance with some embodiments. Further, the user interface may be displayed on a presentation device such as a PC monitor, the HUD device, etc.

Further, in many embodiments, the techniques described herein can provide a practical application and several technological improvements. In one example, the techniques described herein can provide improved efficiency for the user, by providing a method of recording snapshots taken during a procedure that can be saved in a patient file.

In one embodiment, the techniques described herein may facilitate increased safety by use of a Computer Generated Reality (CGR) environment, by providing a virtual screen that cannot be obscured during a procedure in the virtual environment controlled by a voice-based interface. The user has full visibility of diagnostic data and use of hands throughout the procedure.

In one embodiment, the techniques described herein may facilitate increased safety by use of the CGR environment, by providing a customizable placement of a virtual screen and medical vital signs data to accommodate different preferences and requirements of the user.

A computer-readable storage medium storing a program of instructions executable by a machine to perform one or more methods described herein also may be provided. Features as well as the structure and operation of various embodiments are referenced in the accompanying drawings and photographs.

Further, in accordance with the invention, an apparatus, and a method are described herein related to the manipulation by voice commands of one or more data-displaying devices associated with medical data presented in an extended reality type HUD monitor or a projecting screen. Computer-assisted navigation in surgery provides surgeons with enhanced visualization of surgical instruments concerning radiographic images of the patient's anatomy. Other patient data such as vitals and ultrasound images are available for the surgeon in different areas of the surgical room. A surgeon's view of physical monitors during surgery may become obstructed by intervening personnel and/or equipment. However, existing techniques that use one device to supplement the input and output capabilities of another device may be limited with respect to efficiency, usability, or capability for the user experiences.

Further, the apparatus may be a head-mountable device that presents medical data from several devices on the virtual display screen as prompted by the user through a microphone. The user can manipulate data from several devices and request a presentation of the manipulated data on any head-up display screen in any form. The manipulated data can be customized by the user on a PC or on the virtual screen by voice and/or virtual hands. Our apparatus is a wearable device and can be a virtual reality (VR) headset with a microphone affixed to it.

Further, in some embodiments, the apparatus can be an ophthalmic device or an intraocular implant where the medical personnel can obtain data from other ophthalmic devices simultaneously on the head-mountable device during ophthalmic imaging by a voice command.

Further, in another embodiment, a motion tracking glove consisting of different sensors is provided to track the position and orientation of our hand where the user can use their hand gestures to move to the next/previous image on the screen, or/and zoom in/out on the user interface.

Further, in some embodiments, a footswitch can be used to detect foot gestures or any motion input at the feet of the user. The footswitch affixed to our head-mountable device comprises of a medal and the user can press the pedal to zoom in the image on our heads-up display and vice-versa.

Further, in some embodiments, a head-mountable tracking device can be used to move to the next/previous image by moving one's head horizontally left/right. The head-mountable tracking device can be used to detect vertical up/down gestures to respond Yes/No to a prompt on the user interface, say giving a voice command for playing a previously recorded video or for example replying through a voice command for a requested confirmation prompt.

Further, in another embodiment, an eye-tracking implant or device detects the iris of the surgeon for authorized access to the stored surgical procedures and vitals of a patient.

Further, in some embodiments, a camcorder of the head-mountable device records real-time data and captures images during a surgical procedure, and stores it for further use. The user can retrieve the stored videos of surgical procedures for reference. Snapshots can be taken from the played video and further cropped and stored for storing patient's vitals and substantial information for surgical procedures.

Further, in some embodiments, a user can voice a command to change the resolution of the screen as per the convenience of the user. The user may voice a command to switch to a required input to the head-mountable device say, to a PC, smartphone, or/and any external system in the vicinity of the head-mountable device.

Further, in another embodiment, a proximity sensor incorporated in the head-mountable device detects a secondary display device to connect to and stream the live surgical procedure from the first head-mountable device. For instance, surgeons accompanying the user surgeon can also assist by viewing the live surgery on the secondary display device.

Further, in another embodiment, a communication/network module transmits the requested medical data to the secondary display device for streaming the live surgery procedure.

Further, in some embodiments, a network/communication module is used to receive the medical data from a heart rate monitor or a radiography monitor, so that the medical professional can use the patient vitals for future reference.

Further, in some embodiments, the user can voice a command to create one or more menu options for displaying on the user interface. For adding options, the user can add any option for their convenience and customize the drop-down menu or/and the follow-up menu path.

Further, in another embodiment, the user can decide to customize confirmation messages and/or initiate a timer of the overlaying of that message or an image over the existing first area of the head-mountable device. For example, a snapshot of an area of the screen will show a one-second message of confirmation, currently overlaid on the first image on the screen, say, before deleting a piece of medical information.

Further, in another embodiment, the user can toggle between different options on the menu through voice command or a motion-tracking glove. For instance, the user may speak 'open drop-down to update data' for zoom in/out and/or cropping of the medical data.

Further, in some embodiments, a display extraction editor is used to crop and store the images during a real-time surgery. The user may voice a command to crop, move the cropped position, center the image, or overlay it on another, generating a Picture in Picture (Pip). The user may use a motion-tracking glove/virtual hands for navigating and initiating the same choices in the menu.

Further, in another embodiment, a voice engine creator is responsible for the training component. The user speaks a word and a machine-learning algorithm on which the speech trainer is trained, detects one or more aliases of the word, and stores in in word library for repetitive training.

Further, in an embodiment, the speech trainer matches input words to a library of words or suggests aliases for the word. The word library and training results are stored on a memory device operatively coupled to the hardware processor.

Further, in another embodiment, a feedback of the alias stored, correct and incorrect count of words, and a running average of each alias, summarizing the speech trainer metrics is presented on the heads-up display screen of the head-mountable device.

Further, in another embodiment, the word library can be stored in a cloud database and words could be added to it for speech training.

Figure 20:
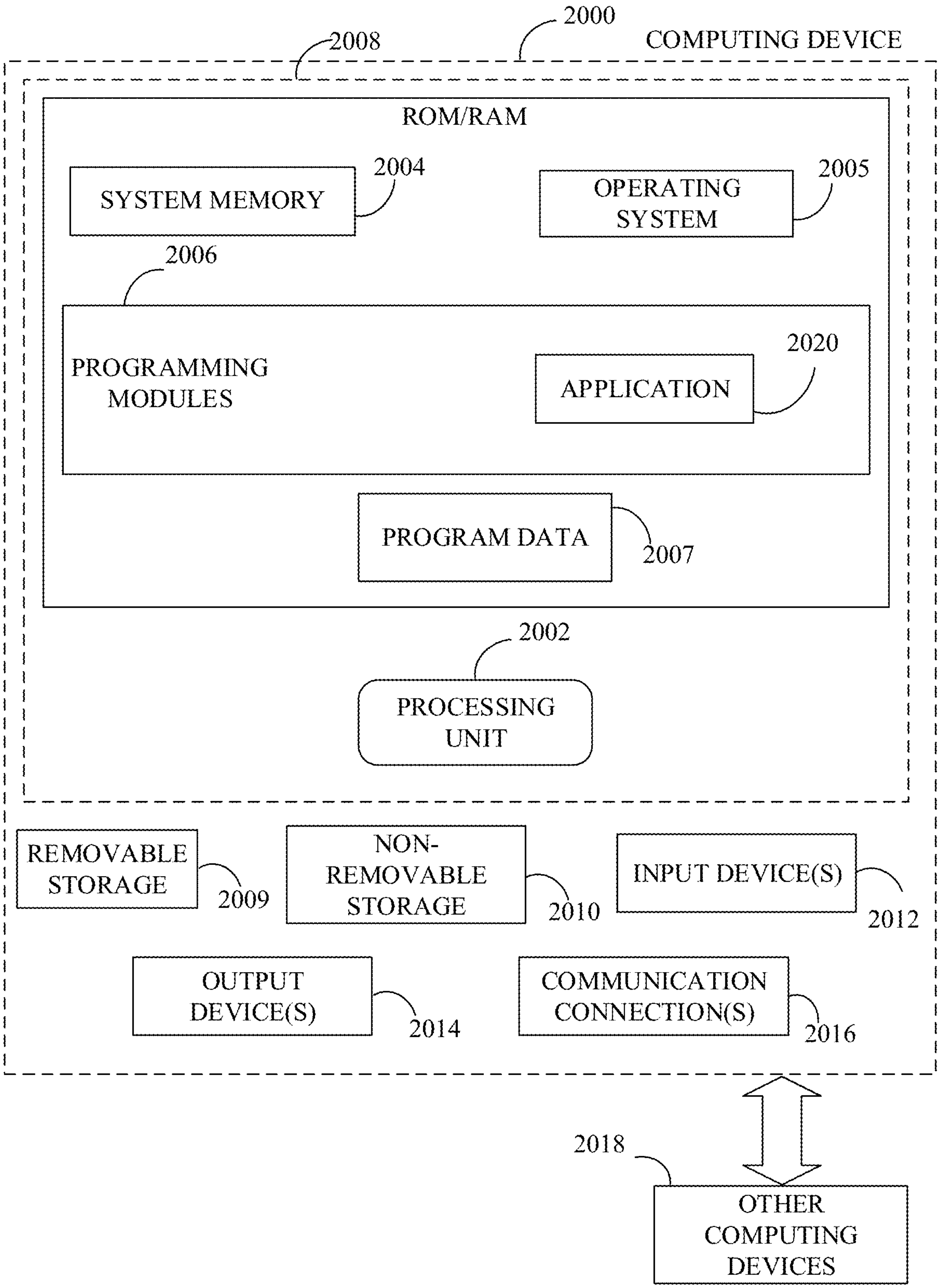
FIG. 20 is a block diagram of a computing device for implementing the methods disclosed herein, in accordance with some embodiments.

With reference to FIG. 20, a system consistent with an embodiment of the disclosure may include a computing device or cloud service, such as computing device 2000. In a basic configuration, computing device 2000 may include at least one processing unit 2002 and a system memory 2004. Depending on the configuration and type of computing device, system memory 2004 may comprise, but is not limited to, volatile (e.g. random-access memory (RAM)), non-volatile (e.g. read-only memory (ROM)), flash memory, or any combination. System memory 2004 may include operating system 2005, one or more programming modules 2006, and may include a program data 2007. Operating system 2005, for example, may be suitable for controlling computing device 2000's operation. In one embodiment, programming modules 2006 may include image-processing modules, machine learning modules, etc. Furthermore, embodiments of the disclosure may be practiced in conjunction with a graphics library, other operating systems, or any other application program and is not limited to any particular application or system. This basic configuration is illustrated in FIG. 20 by those components within a dashed line 2008.

Computing device 2000 may have additional features or functionality. For example, computing device 2000 may also include additional data storage devices (removable and/or non-removable) such as, for example, magnetic disks, optical disks, or tape. Such additional storage is illustrated in FIG. 20 by a removable storage 2009 and a non-removable storage 2010. Computer storage media may include volatile and non-volatile, removable, and non-removable media implemented in any method or technology for storage of information, such as computer-readable instructions, data structures, program modules, or other data. System memory 2004, removable storage 2009, and non-removable storage 2010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD), other optical storage, magnetic cassettes, magnetic tape, magnetic disk storage or other magnetic storage devices, or any other medium which can be used to store information and which can be accessed by computing device 2000. Any such computer storage media may be part of device 2000. Computing device 2000 may also have input device(s) 2012 such as a keyboard, a mouse, a pen, a sound input device, a touch input device, a location sensor, a camera, a biometric sensor, etc. Output device(s) 2014 such as a display, speakers, a printer, etc. may also be included. The aforementioned devices are examples and others may be used.

Computing device 2000 may also contain a communication connection 2016 that may allow device 2000 to communicate with other computing devices 2018, such as over a network in a distributed computing environment, for example, an intranet or the Internet. Communication connection 2016 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 2004, including operating system 2005. While executing on processing unit 2002, programming modules 2006 (e.g., application 2020 such as a media player) may perform processes including, for example, one or more stages of methods, algorithms, systems, applications, servers, databases as described above. The aforementioned process is an example, and processing unit 2002 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. An apparatus for facilitating presentation of medical data from a plurality of data displays to a clinician during a medical procedure or a surgical procedure, the apparatus comprising:

at least one of a microphone and a hand tracking device associated with the clinician, wherein the microphone is configured for generating a sound data and the hand tracking device is configured for generating a gesture data based on a hand gesture where the sound data and the gesture data are based on a command from the clinician;

a processing device communicatively coupled with at least one of the microphone and the hand tracking device, wherein the processing device is configured for:

analyzing at least one of the sound data and the gesture data;

generating an instruction based on the analyzing to perform at least one operation; and performing the command by carrying out the at least one operation that extracts a portion of at least one medical data, that is identified and selected by the clinician from one of the plurality of data displays by cropping specific parts of the at least one medical data as an image, and places the image in a customizable position on a customized display; and repositioning and resizing the image and overlaying the image in the customizable position over a second image of the at least one medical data, and moving at least the image using the sound data or the gesture data in a virtual screen to permit the clinician to produce the customized display on at least one of a head-mountable device, an ophthalmic device, and an implantable device;

at least one of the head-mountable device, the ophthalmic device, and the implantable device communicatively coupled with the processing device, wherein each of the head-mountable device, the ophthalmic device, and the implantable device comprises at least one of a display device and a sound production device, wherein at least one of the head-mountable device, the ophthalmic device, and the implantable device is configured for presenting the customized display on the virtual screen.

2. The apparatus of claim 1, being a wearable device.

3. The apparatus of claim 1, being an extended reality device.

4. The apparatus of claim 1, wherein the hand tracking device comprises a motion tracking glove configured for generating the gesture data by tracking the hand gesture of the clinician associated with the apparatus.

5. The apparatus of claim 1, further comprising a storage device, where the at least one operation further comprises storing of the image on the storage device.

6. The apparatus of claim 1, wherein at least one of the head-mountable device, the ophthalmic device, and the implantable device comprises a heads-up display screen, wherein the at least one operation further comprises at least one of causing selecting of at least one of a screen type and a screen input associated with the heads-up display screen, and creating one or more options of a menu for the heads-up display screen; and overlaying a first menu over a second menu on the heads-up display screen.

7. The apparatus of claim 6, wherein the at least one operation further comprises creating a custom path for the one or more options of the menu.

8. The apparatus of claim 6, wherein the at least one operation further comprises at least one of causing displaying and navigating between the one or more options of the menu.

9. The apparatus of claim 1, further comprising a footswitch configured for generating a foot gesture data representing one or more foot gestures of the clinician, wherein the footswitch is communicatively coupled with the processing device, wherein the processing device is further configured for analyzing the foot gesture data, wherein the generating of the instruction is further based on the analyzing of the foot gesture data.

10. The apparatus of claim 1, further comprising an eye tracking device configured for generating an eye gesture data representing one or more eye gestures of the clinician, wherein the eye tracking device is communicatively coupled with the processing device, wherein the processing device is further configured for analyzing the eye gesture data, wherein the generating of the instruction is further based on the analyzing of the eye gesture data.

11. The apparatus of claim 1, further comprising a communication device configured for receiving the at least one medical data from an external medical system, wherein the communication device is communicatively coupled with a storage device.

12. The apparatus of claim 11, wherein the communication device is further configured for transmitting the at least one medical data to a secondary presentation device comprising at least one of a secondary display device and a secondary sound production device.

13. The apparatus of claim 12, further comprising a proximity sensor communicatively coupled with at least one of the head-mountable device, the ophthalmic device, and the implantable device, wherein the proximity sensor is configured for detecting a presence of the secondary presentation device comprising at least one of the display device and the sound production device in a vicinity of the apparatus, wherein the transmitting of the at least one medical data is based on the detecting of the presence of the secondary presentation device.

14. The apparatus of claim 1, wherein the analyzing of the at least one of the sound data and the gesture data is based on a machine learning model.

15. An apparatus for facilitating presentation of medical data from a plurality of data displays to a clinician during a medical procedure or surgical procedure, the apparatus comprising:

at least one of a microphone and a hand tracking device associated with the clinician, wherein the microphone is configured for generating a sound data and the hand tracking device is configured for generating a gesture data based on a hand gesture wherein the hand tracking device comprises a motion tracking glove configured for generating the gesture data by tracking the hand gesture of the clinician associated with the apparatus, and wherein the sound data and the gesture data are based on a command from the clinician, and;

a processing device communicatively coupled with at least one of the microphone and the hand tracking device, wherein the processing device is configured for:

analyzing at least one of the sound data and the gesture data;

generating an instruction based on the analyzing to perform at least one operation; and performing the at least one operation that extracts a portion of at least one medical data, that is identified and selected by the clinician from one of the plurality of data displays by cropping specific parts of the at least one medical data as an image, and places the image in a customizable position on a customized display; and repositioning and resizing the image and overlaying the image in the customizable position over a second image of the at least one medical data, and moving at least the image using the sound data or the gesture data in a virtual screen to permit the clinician to produce the customized display on at least one of a head-mountable device, an ophthalmic device, and an implantable device; and at least one of the head-mountable device, the ophthalmic device, and the implantable device communicatively coupled with the processing device, wherein each of the head-mountable device, the ophthalmic device, and the implantable device comprises at least one of a display device and a sound production device, wherein at least one of the head-mountable device, the ophthalmic device, and the implantable device is configured for presenting the customized display on the virtual screen.

* * * * *